(12) United States Patent
Ueno et al.

(10) Patent No.: US 7,896,851 B2
(45) Date of Patent: *Mar. 1, 2011

(54) CATHETER WITH PUNCTURE SENSOR

(75) Inventors: Takafumi Ueno, Fukuoka (JP); Takashi Yamamoto, Ebira (JP); Yoshitaka Oomura, Hadano (JP); Tetsuo Tanaka, Setagaya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1493 days.

This patent is subject to a terminal disclaimer.

(21) Appl. No.: 10/808,312

(22) Filed: Mar. 25, 2004

(65) Prior Publication Data

US 2004/0249295 A1    Dec. 9, 2004

(30) Foreign Application Priority Data

Mar. 28, 2003   (JP) .............................. 2003-090225

(51) Int. Cl.
*A61M 5/00*    (2006.01)
*A61B 5/04*    (2006.01)

(52) U.S. Cl. ...................................... 604/264; 600/509
(58) Field of Classification Search .................. 604/264
See application file for complete search history.

(56) References Cited

U.S. PATENT DOCUMENTS

| | | | |
|---|---|---|---|
| 5,078,714 A | 1/1992 | Katims | |
| 5,405,376 A | 4/1995 | Mulier et al. | |
| 5,568,809 A | 10/1996 | Ben-haim | |
| 5,797,870 A | 8/1998 | March et al. | |
| 5,931,810 A | 8/1999 | Grabek | |
| 5,972,013 A | 10/1999 | Schmidt | |
| 6,059,726 A | 5/2000 | Lee et al. | |
| 6,063,078 A | 5/2000 | Wittkampf | |
| 6,086,582 A | 7/2000 | Altman et al. | |
| 6,102,887 A | 8/2000 | Altman | |
| 6,106,524 A * | 8/2000 | Eggers et al. ................. | 606/50 |
| 6,165,164 A | 12/2000 | Hill et al. | |

(Continued)

FOREIGN PATENT DOCUMENTS

EP    1264610 A1    12/2002

(Continued)

OTHER PUBLICATIONS

Communication from the European Patent Office dated Jan. 18, 2007 enclosing extended European Search Report.

(Continued)

*Primary Examiner*—Nicholas D Lucchesi
*Assistant Examiner*—Jason Flick
(74) *Attorney, Agent, or Firm*—Buchanan Ingersoll & Rooney PC

(57) ABSTRACT

Disclosed is a catheter to be percutaneously inserted into a living body lumen, which includes a sheath portion having a lumen extending therein, an insertion member slidably disposed in the lumen of the sheath portion and having a distal end portion capable of protruding from a distal end portion of the sheath portion, an injection needle disposed at the distal end portion of the insertion member for injecting a therapeutic composition into a target tissue, and an electrode disposed at a distal end portion of the catheter for measuring a cardiac action potential.

18 Claims, 15 Drawing Sheets

U.S. PATENT DOCUMENTS

| | | |
|---|---|---|
| 6,190,360 B1 | 2/2001 | Iancea et al. |
| 6,254,573 B1 | 7/2001 | Haim et al. |
| 6,309,370 B1 * | 10/2001 | Haim et al. .................. 604/66 |
| 6,391,005 B1 * | 5/2002 | Lum et al. .................. 604/117 |
| 6,592,552 B1 | 7/2003 | Schmidt |
| 6,623,474 B1 | 9/2003 | Ponzi |
| 7,322,960 B2 | 1/2008 | Yamamoto et al. |
| 2001/0031942 A1 | 10/2001 | Tollner et al. |
| 2002/0183738 A1 | 12/2002 | Chee et al. |
| 2003/0028172 A1 | 2/2003 | Epstein et al. |
| 2003/0032936 A1 | 2/2003 | Lederman |

FOREIGN PATENT DOCUMENTS

| | | |
|---|---|---|
| JP | 04-231068 | 8/1992 |
| JP | 07-088093 A | 4/1995 |
| JP | 09-140802 A | 6/1997 |
| JP | 09-140803 | 6/1997 |
| JP | 11-285534 A | 10/1999 |
| JP | 11-309124 | 11/1999 |
| JP | 2000-024120 A | 1/2000 |
| JP | 2002-28247 | 1/2002 |
| JP | 2002-512552 | 4/2002 |
| WO | WO 94/00050 | 1/1994 |
| WO | WO 98/48722 | 11/1998 |
| WO | WO 99/04851 | 2/1999 |
| WO | WO 9904851 A1 * | 2/1999 |

OTHER PUBLICATIONS

European Patent Office, Jul. 29, 2004 Office Action.
Notification of Reason for Refusal in JP 2003-090225 dated May 13, 2008, and English Translation thereof.
Notice of Reasons for Refusal dated Nov. 25, 2008 in JP 2003-090225.
Official Decision of Refusal in JP2003-090225, dated Jun. 30, 2009, and English translation thereof.
Official Decision to Dismiss the Amendment in JP2003-090225, dated Jun. 30, 2009, and English translation thereof.
Official Notice of Interrogation issued Sep. 7, 2010 by the Japanese Patent Office in Japanese Patent Application No. 2003-90225 and English translation thereof.

* cited by examiner

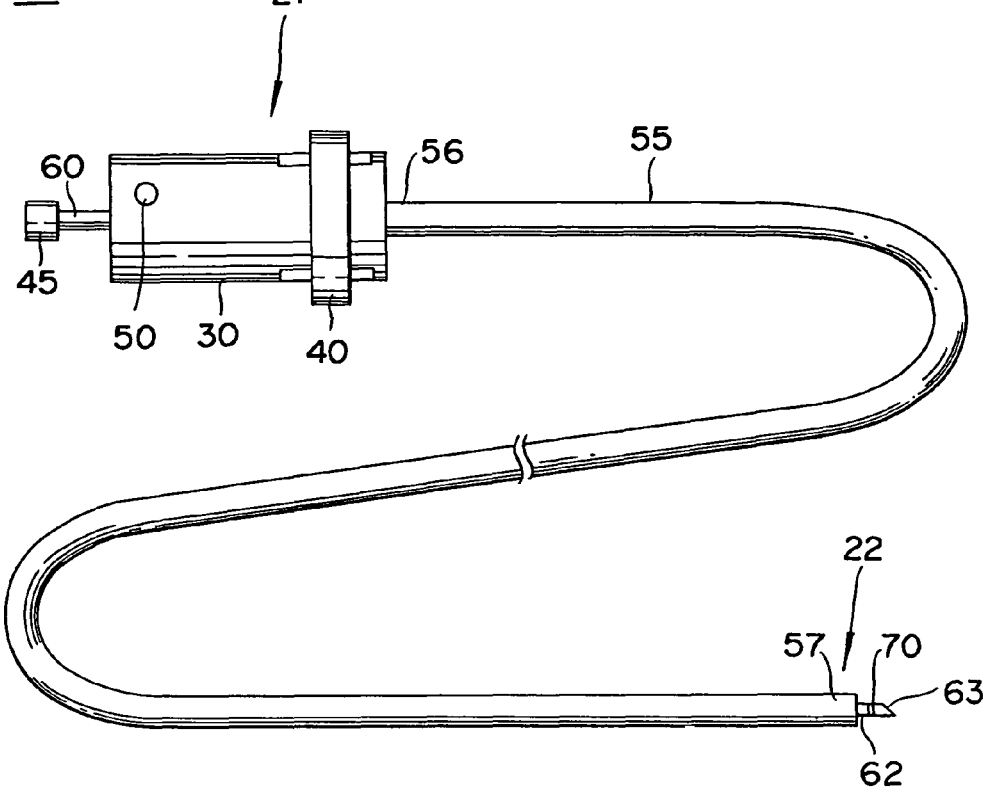
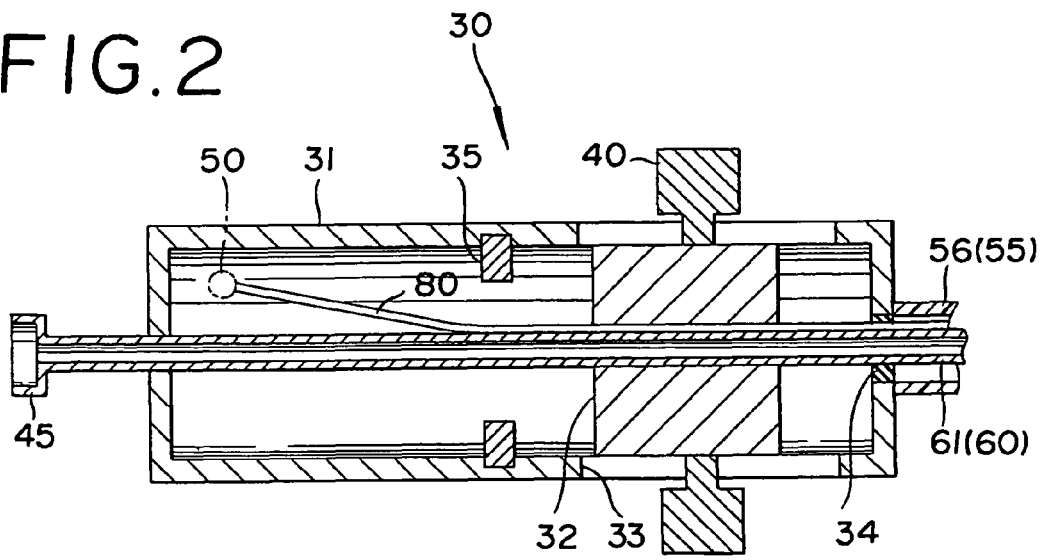

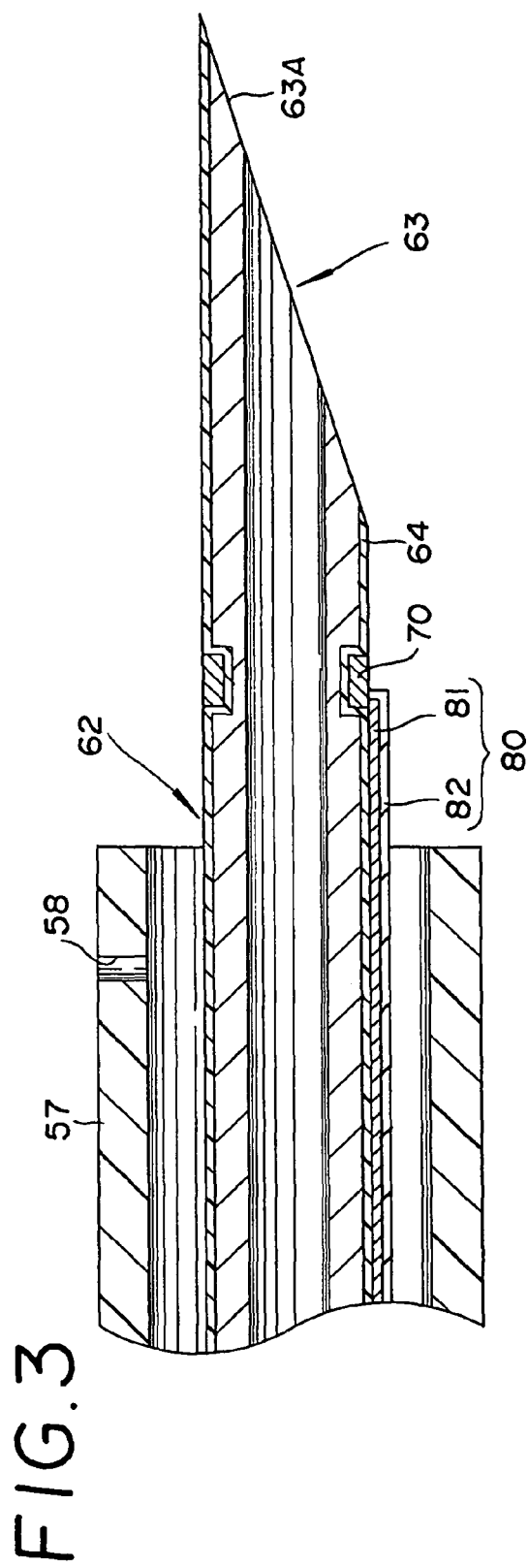
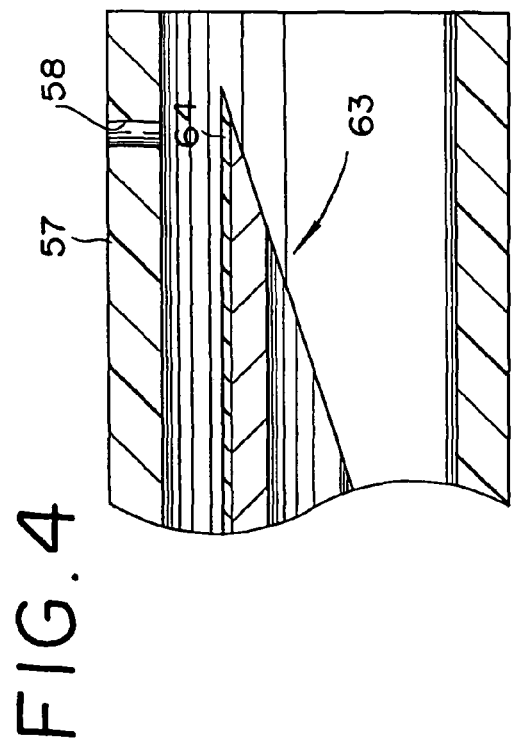
FIG. 3
FIG. 4

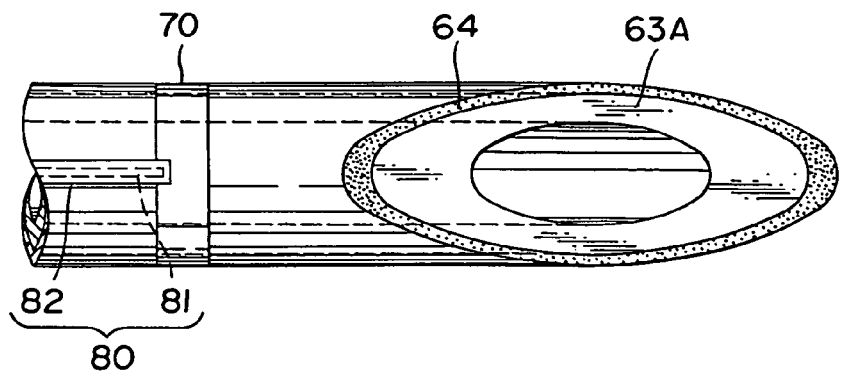
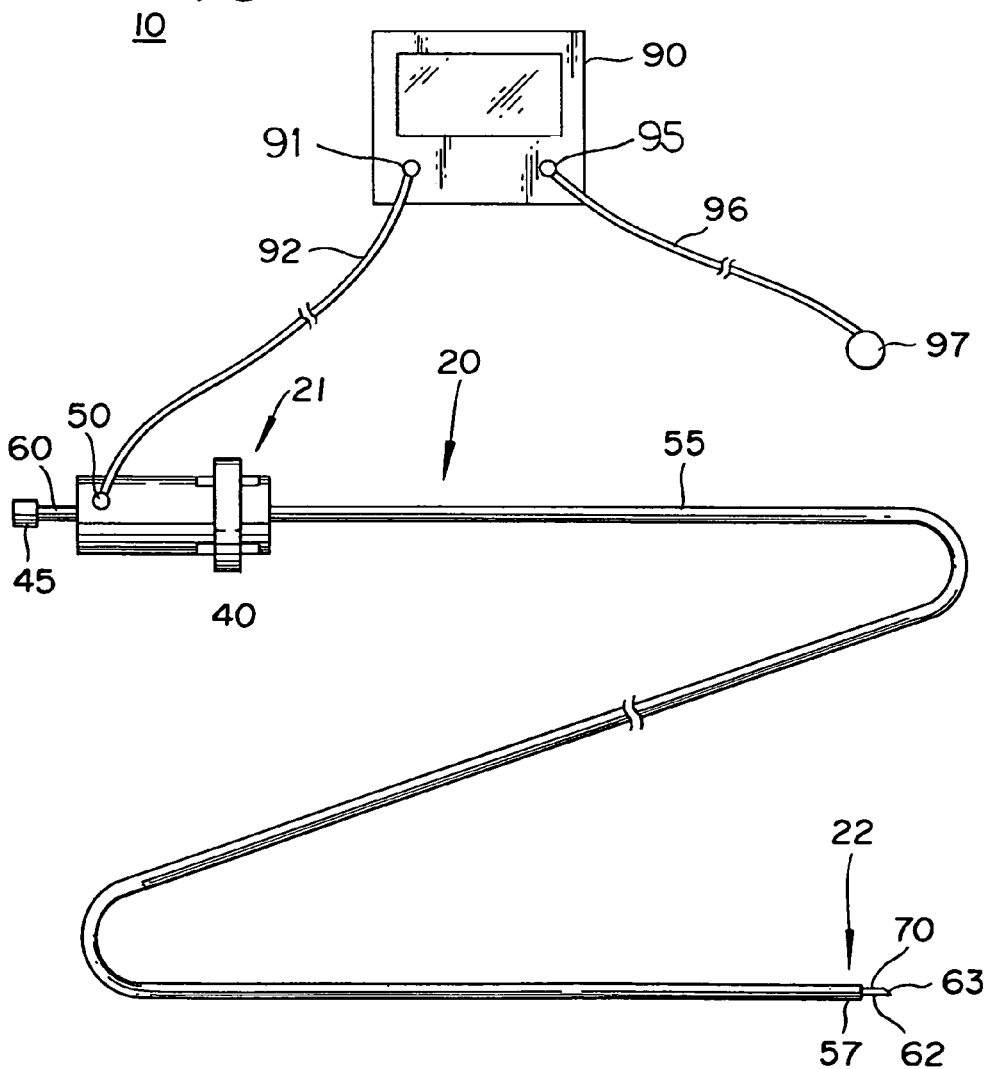

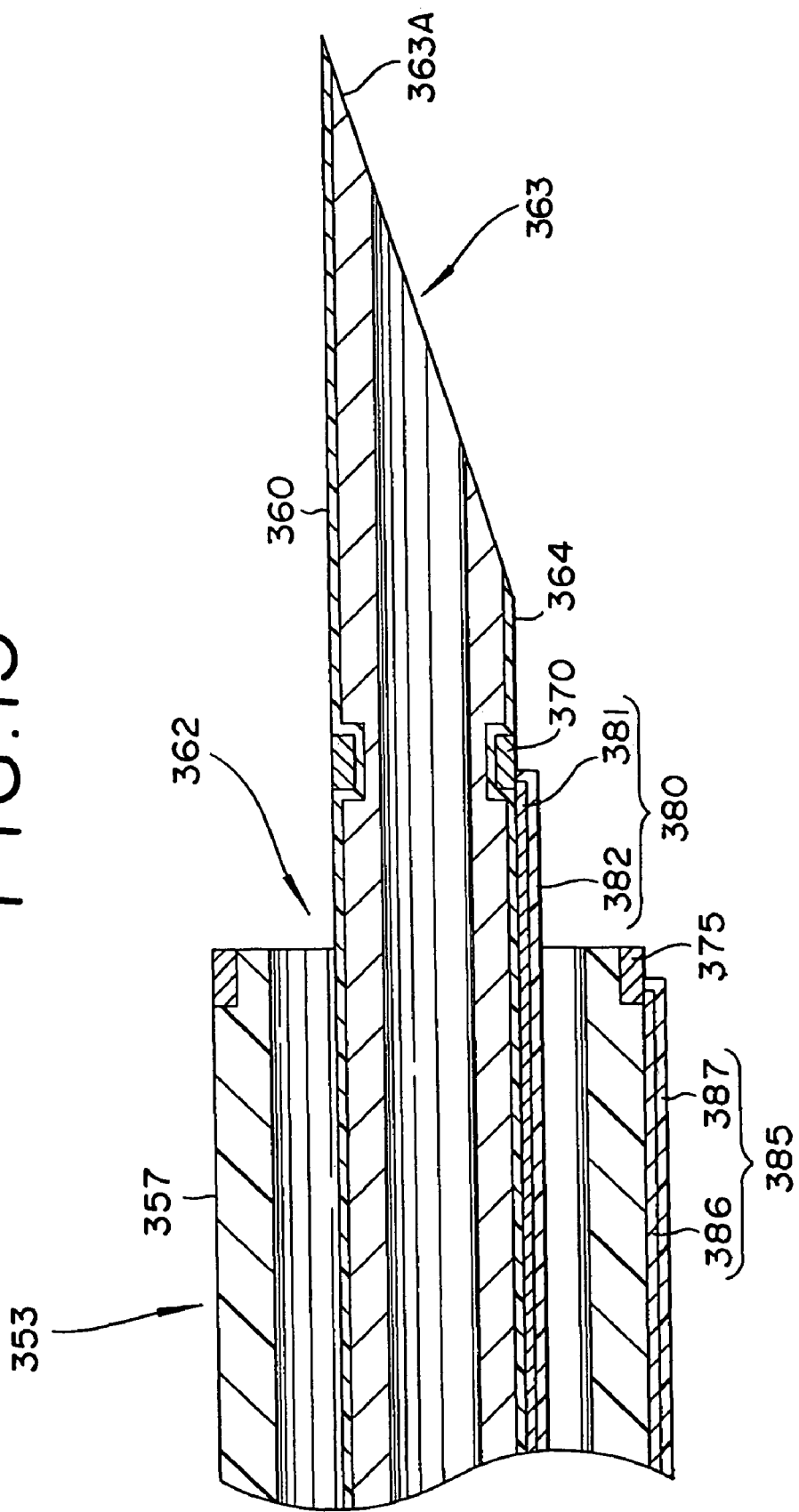

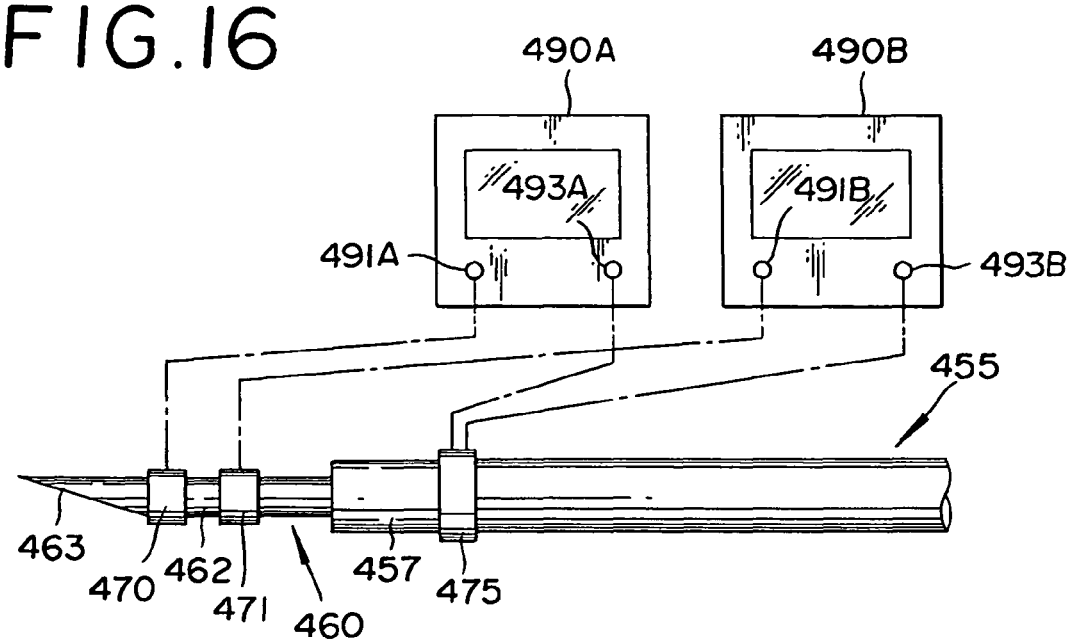
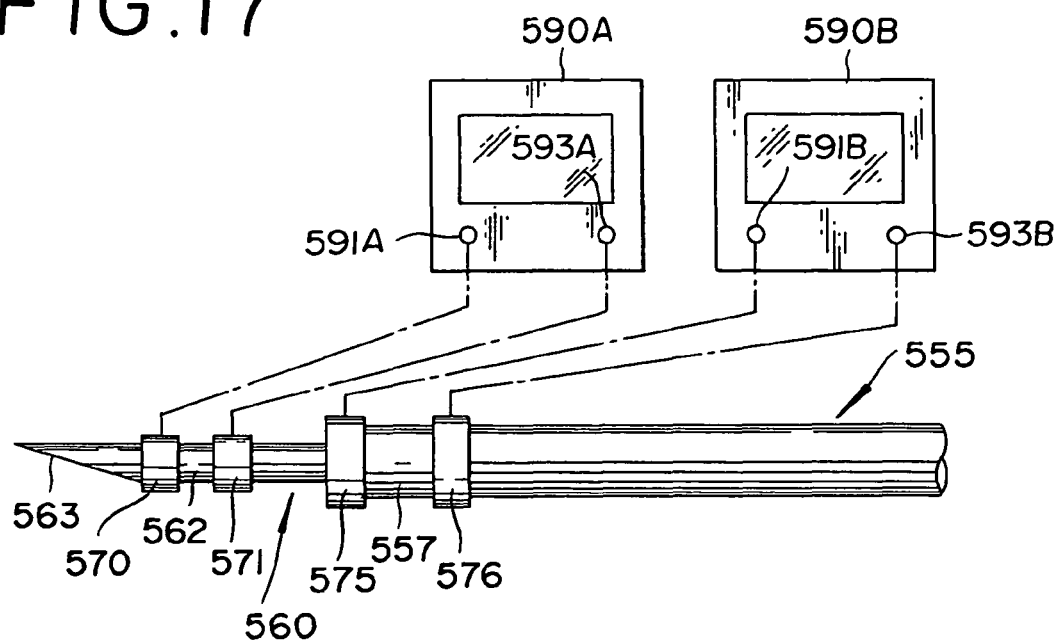

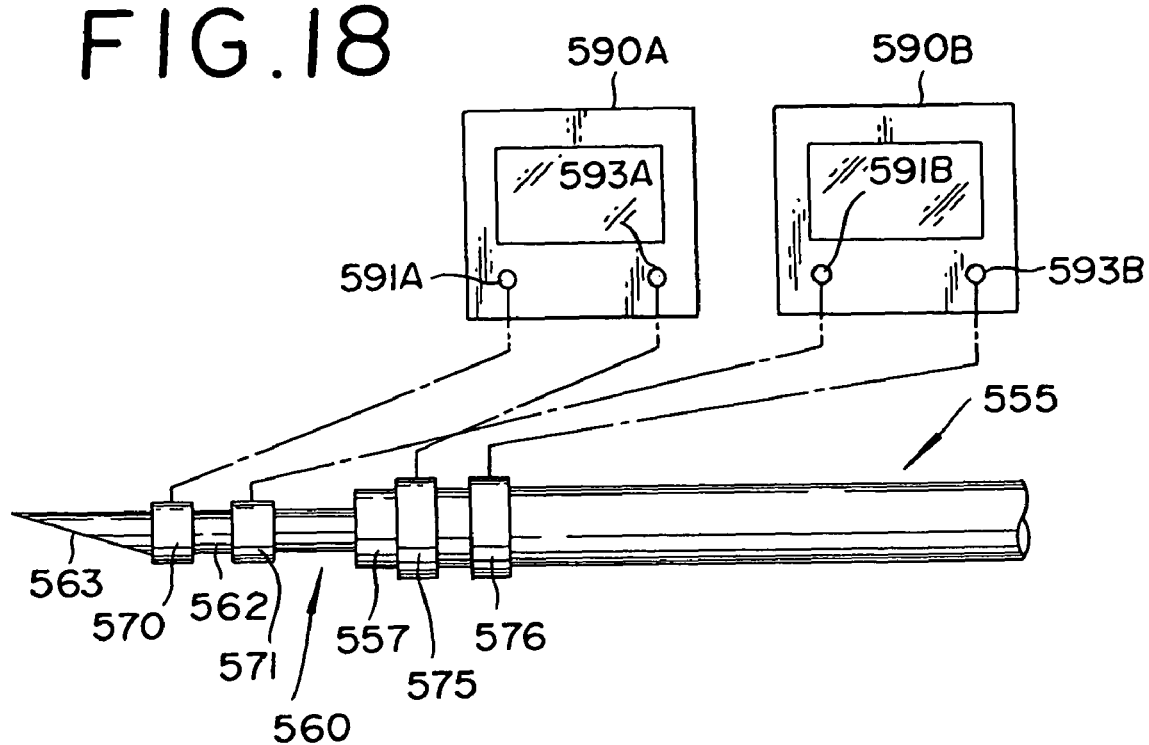

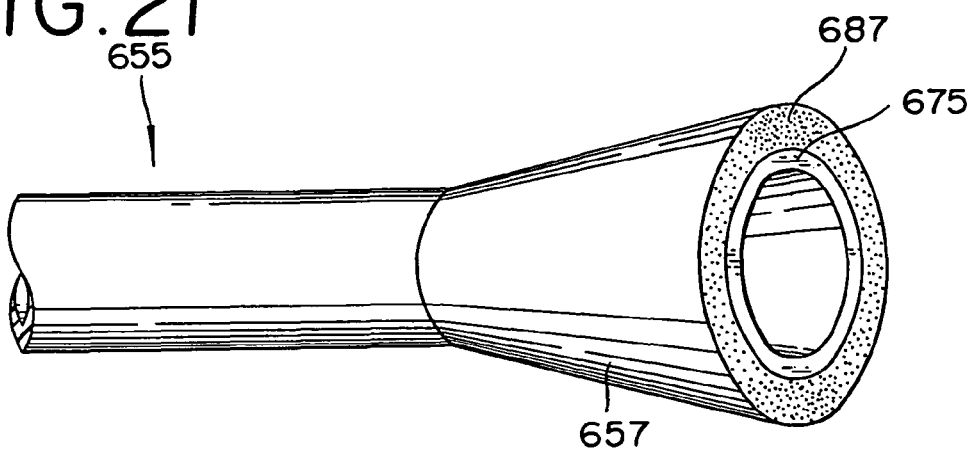
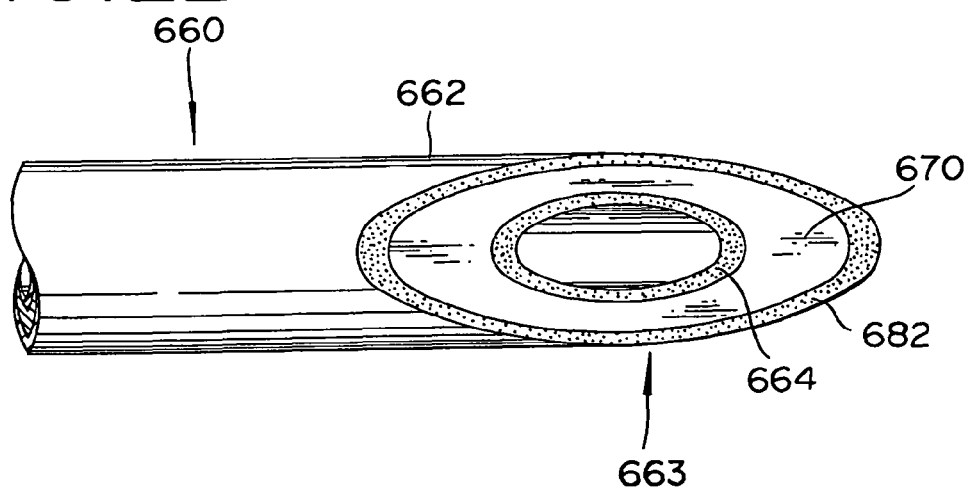
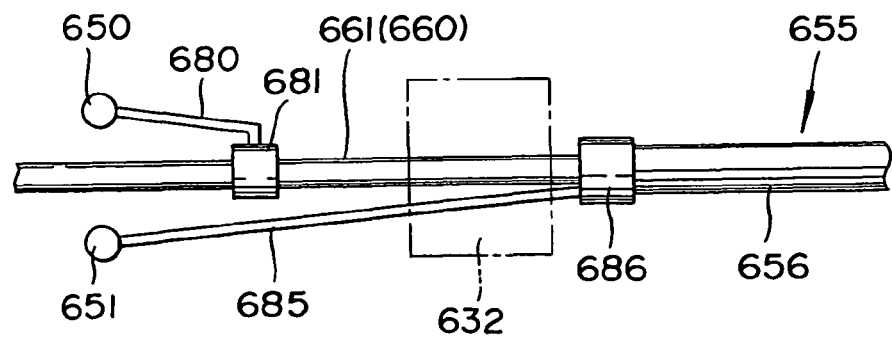

CATHETER WITH PUNCTURE SENSOR

BACKGROUND OF THE INVENTION

1. Field of the Invention

The present invention relates to a catheter for injecting a therapeutic composition into a diseased part in a living body, particularly a cardiac ischemic part, or the surrounding portion thereof.

2. Description of the Related Art

The number of the patients of cardiac ischemic diseases has been increasing attendant on the increase of causes of danger, such as westernization of dietary life and the increase of social stresses. Particularly, the increase in the number of the patients of grave heart failure has come to be a serious problem in the developed countries; in the world, for example, no less than 15 million new patients have been generated yearly.

As a therapy for the cardiac ischemic diseases, gene therapy and cellular therapy have been being investigated. Conventional catheters applicable to such therapeutic approaches are provided at its distal end with an injection needle for injecting a therapeutic composition. For example, they are disclosed in U.S. Pat. No. 5,405,376 (corresponding to Japanese Unexamined Patent Publication No. Hei 8-508917) (Patent Reference 1), U.S. Pat. No. 5,797,870 (Patent Reference 2), U.S. Pat. No. 6,254,573 (Patent Reference 3), U.S. Pat. No. 6,309,370 (corresponding to Japanese Patent Laid-open No. 2001-87392) (Patent Reference 4), U.S. Pat. No. 5,972,013 (Patent Reference 5), U.S. Pat. No. 6,592,552 (corresponding to Japanese Unexamined Patent Publication No. 2001-516625) (Patent Reference 6), U.S. Pat. No. 5,931,810 (Patent Reference 7) and U.S. Pat. No. 6,102,887 (Patent Reference 8).

Specifically, Patent References 1 and 2 each disclose a catheter including a spirally formed injection needle. Patent References 3 and 4 each disclose a catheter including a contact-type sensor composed of a pressure sensor at a distal end portion thereof.

Patent References 5 and 6 each disclose a catheter including a mechanism for providing a negative pressure in the inside thereof so as to fix a distal end portion thereof to a tissue under suction. Patent Reference 7 discloses a puncture device for puncturing by mechanically gripping a tissue and fixing a distal end portion of the catheter to the tissue.

Patent Reference 8 discloses a catheter which includes an injection needle capable of being contained in a distal end portion thereof, and a fixing device to be opened radially outwards from the distal end portion. Incidentally, Patent Reference 8 discloses both a fixing device with sharp tips and a fixing device without sharp tips.

However, the catheters disclosed in the above patent references have the problems as follows. The spiral needle according to Patent References 1 and 2 has the merit that at the time of injecting a therapeutic composition into a tissue, the spiral needle does not slip off from the tissue and assured injection is possible, but the spiral needle has the demerit that it cannot be drawn out easily. Therefore, for example, in the condition where the spiral needle is puncturing a fragile myocardial infarction tissue, an erroneous movement of a distal end portion of the catheter may lead to the tear-off of the myocardial tissue by the spiral needle.

The contact-type sensor according to Patent References 3 and 4 is disposed at an end face of a distal end portion of the catheter and needs to be brought into assured contact with the myocardial tissue. Since the inside of a heart is highly rugged, however, the contact-type sensor is liable to generate errors and, therefore, is questionable about accuracy.

The catheter according to Patent References 5 and 6 is intended for use at a flat part which is not filled with a humor such as blood. Where the catheter is applied to a tissue surface which is filled with a humor and which is not necessarily flat, therefore, it is difficult to bring the distal end portion of the catheter into perfect contact with the tissue surface, and the catheter may suck the humor in.

The puncture device according to Patent Reference 7 is intended for gripping a comparatively strong heart. Therefore, where the puncture device is applied to a fragile tissue, for example, a myocardial infarction tissue, the puncture device may tear off the tissue.

The fixing device with sharp tips according to Patent Reference 8 makes it possible to fix the catheter to a tissue at the time of puncturing the tissue and injecting a therapeutic composition into the tissue. However, the fixing device is designed to be radially enveloped after puncturing the target tissue and, therefore, it is very high in invasiveness to the surrounding part of the target tissue. The fixing device without sharp tips according to Patent Reference 8 is designed for fixing the catheter to a tissue by spreading out trabeculae carneae in a heart. With the fixing device, therefore, it is very difficult to operate the catheter, and it is impossible to fix the catheter to an arbitrary part in the heart.

SUMMARY OF THE INVENTION

The present invention has been made in order to solve the above-mentioned problems in the prior art. Accordingly, it is an object of the present invention to provide a catheter, and a catheter system, which is low in invasiveness and which makes it possible to securely achieve puncture of a target tissue by an injection needle and injection of a therapeutic composition into the target tissue.

It is another object of the present invention to provide a method for securely achieving puncture of a target tissue in a living body by an injection needle and injection of a therapeutic composition into the target tissue, with little invasion.

In order to attain the above objects, the present invention resides in the following.

A catheter to be percutaneously inserted into a living body lumen, the catheter including: a sheath portion having a lumen extending therein, an insertion member slidably disposed in the lumen of the sheath portion and having a distal end portion capable of protruding from a distal end portion of the sheath portion, an injection needle disposed at the distal end portion of the insertion member for injecting a therapeutic composition into a target tissue in a living body, and an electrode disposed at a distal end portion of the catheter for measuring a cardiac action potential.

A catheter system including: a catheter to be percutaneously inserted into a living body lumen, the catheter including a sheath portion having a lumen extending therein, an insertion member slidably disposed in the lumen of the sheath portion and having a distal end portion capable of protruding from a distal end portion of the sheath portion, and an injection needle disposed at the distal end portion of the insertion member for injecting a therapeutic composition into a target tissue in a living body; a first electrode disposed at a distal end portion of the catheter for measuring a cardiac action potential; a second electrode for measuring the cardiac action potential; and a puncture detection unit to which a conductor extending from the first electrode and a conductor extending from the second electrode are connected and which detects puncture by the injection needle based on the cardiac action potential measured by the first electrode and the second electrode.

The method of injecting a therapeutic composition by use of a catheter to be percutaneously inserted into a living body lumen, the catheter including a sheath portion having a lumen extending therein, an insertion member slidably disposed in the lumen of the sheath portion and having a distal end portion capable of protruding from a distal end portion of the sheath portion, an injection needle disposed at the distal end portion of the insertion member for injecting the therapeutic composition into a target tissue, and an electrode disposed at a distal end portion of the catheter for measuring a cardiac action potential, the method including the steps of: (a) inserting the catheter into a living body and advancing the catheter to the vicinity of the target tissue; and (b) puncturing the target tissue by the injection needle and injecting the therapeutic composition into the target tissue through the injection needle, based on the cardiac action potential measured by the electrode.

According to the present invention, it is possible to provide a catheter and a catheter system with which it is possible to securely attain puncture of a target tissue by an injection needle and injection of a therapeutic composition, with low invasiveness. In addition, according to the present invention, it is possible to provide a method of injecting a therapeutic composition by use of a catheter with which it is possible to securely attain puncture of a target tissue by an injection needle and injection of a therapeutic composition.

BRIEF DESCRIPTION OF THE DRAWINGS

The above and other objects, features and advantages of the present invention will become apparent from the following description and appended claims, taken in conjunction with the accompanying drawings.

FIG. 1 is a schematic view of a catheter according to Embodiment 1.

FIG. 2 is a sectional view for illustrating an operating unit shown in FIG. 1.

FIG. 3 is a sectional view for illustrating a distal end portion of the catheter shown in FIG. 1, showing the condition where an injection needle is protruding.

FIG. 4 is a sectional view for illustrating the distal end portion of the catheter shown in FIG. 1, showing the condition where the injection needle is retracted.

FIG. 5 is a side view of a distal end portion of an insertion member of the catheter shown in FIG. 1.

FIG. 6 is a schematic view for illustrating a catheter system to which the catheter shown in FIG. 1 is applied;

FIG. 15 is a sectional view for illustrating a catheter according to Embodiment 3.

FIG. 16 is a schematic view for illustrating a catheter system according to Embodiment 4.

FIG. 17 is a schematic view for illustrating a catheter system according to Embodiment 5.

FIG. 18 is a schematic view for illustrating a modification of the catheter system according to Embodiment 5.

FIG. 21 is a side view for illustrating an example of a method of manufacturing a sheath portion where an electrode is disposed.

FIG. 22 is a side view for illustrating an example of a method of manufacturing an insertion member where an electrode is disposed.

FIG. 23 is a schematic view for illustrating the structures of a proximal end portion of the sheath portion shown in FIG. 21 and a proximal end portion of the insertion portion shown in FIG. 22.

DETAILED DESCRIPTION OF THE PREFERRED EMBODIMENTS

Figure 7:
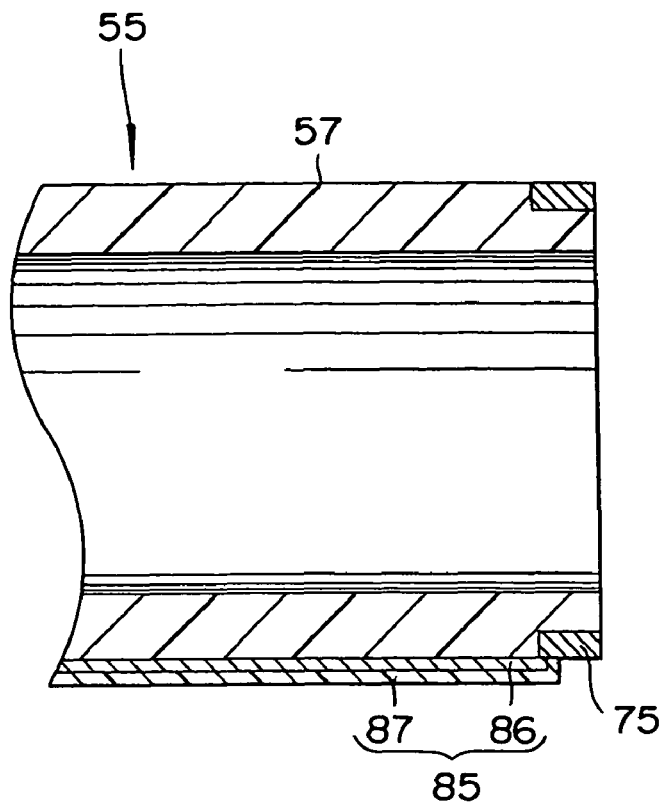
FIG. 7 is a sectional view of a distal end portion of a sheath portion, for illustrating a modification of the catheter according to Embodiment 1.

Now, embodiments of the present invention will be described in detail below, referring to the drawings.

As shown in FIG. 1, a catheter 20 according to Embodiment 1 includes an operating unit 30, a sheath portion 55, an injection needle 63 disposed at a distal end portion 62 of an insertion member 60, and an electrode 70, and is used in the state of being percutaneously inserted in a living body lumen. Incidentally, the electrode 70 is disposed at the distal end portion 62 of the insertion member 60, is used for measuring a cardiac action potential (electrocardio), and functions as a puncture sensor.

The operating unit 30 is located at a proximal end portion 21 of the catheter 20, and the distal end portion 62 of the insertion member 60 and the injection needle 63 are located at a distal end portion 22 of the catheter 20.

The sheath portion 55 has a lumen extending therein, in which the insertion member 60 extends slidably. The shape of the sheath portion 55 is not particularly limited, but is preferably a hollow cylindrical shape. The outside diameter of the sheath portion 55 is not particularly limited, but is preferably not more than 10 french (3.3 mm).

The material of the sheath portion 55 is not particularly limited; usable examples of the material include polymeric materials such as polyolefins, olefin-based elastomers, polyesters, soft polyvinyl chloride, polyurethane, urethane-based elastomers, polyamides, amide-based elastomers, polytetrafluoroethylene, fluororesin elastomers, polyimides, ethylene-vinyl acetate copolymer, and silicone rubbers.

The polyolefins are, for example, polypropylene and polyethylene. The olefin-based elastomers are, for example, polyethylene elastomer and polypropylene elastomer. The amide-based elastomers are, for example, polyamide elastomers.

Where the sheath portion 55 is formed of a synthetic resin, it is possible to enhance the rigidity thereof, for example, by utilizing a superelastic alloy pipe or a metallic embedded coil or embedded mesh.

A distal end portion 57 of the sheath portion 55 preferably has the function as a x-ray contrast marker, and can be formed by use of a resin containing a radiopaque material, for example. Examples of the radiopaque material include powders of tantalum, tungsten carbide, bismuth oxide, barium sulfate, platinum or alloys thereof, cobalt alloys, etc.

The shape of the insertion member 60 is not particularly limited, but is preferably a hollow cylindrical shape. The outside diameter of the insertion member 60 is not particularly limited, inasmuch as the insertion member 60 can be slid in the lumen of the sheath portion 55; the outside diameter is preferably 0.3 to 1.0 mm. The inside diameter of the insertion member 60 is preferably 0.15 to 0.8 mm.

The material of the insertion member 60 is not particularly limited, applicable examples of the material including metals such as stainless steel, Ni—Ti alloy, Cu—Zn alloy, cobalt alloys, tantalum, etc., polyamides, polyimides, ultra-high molecular weight polyethylene, polypropylene, fluororesins, and appropriate combinations thereof.

The injection needle 63 is used for injecting a therapeutic composition into a target tissue. The target tissue is a diseased part in a living body, for example, a cardiac tissue such as a cardiac ischemic part and the surroundings thereof. The injection needle 63 may be constituted, for example, by subjecting the distal end portion 62 of the insertion member 60 to a needle-forming processing to form a bevel (cutting edge surface) or by attaching a separate injection needle to the distal end portion 62 of the insertion member 60.

Next, referring to FIGS. 2 to 5, the proximal end portion 21 and the distal end portion 22 of the catheter 20 will be described in detail.

The operating unit 30 located at the proximal end portion 21 of the catheter 20 includes a housing 31 provided with a slit 33, an output terminal 50 for connection to an external vital amplifier (puncture detection unit), and a hub 45, as shown in FIG. 2.

The output terminal 50 is connected to the electrode 70 disposed at the distal end portion 22 of the catheter 20, through a wire 80 extending along the insertion member 60. The hub 45 is a connector for injection of a therapeutic composition, and, for example, a syringe containing the therapeutic composition is connected thereto.

A proximal end portion 56 of the sheath portion 55 is fixed to the housing 31, whereas a proximal end portion 61 of the insertion member 60 is introduced into the inside of the housing 31 and connected to the hub 45. A drive portion 32 formed of an elastic material is slidably in close contact with the inside surface of the housing 31.

The drive portion 32 includes a central portion to which the insertion member 60 passing therethrough is adhered and fixed, and an outer circumferential portion to which a needle control portion 40 is fixed. The needle control portion 40 is slidably fitted in the slit 33 formed in the housing 31.

Therefore, with the drive portion 32 moved by operating the needle control portion 40, the insertion member 60 is driven. As a result, the injection needle 63 disposed at the distal end portion 62 of the insertion member 60 is protruded from the distal end portion 57 of the sheath portion 55 (see FIG. 3) or is retracted into the distal end portion 57 of the sheath portion 55 (see FIG. 4).

The drive portion 32 is formed of an elastic material, and is disposed in close contact with the inside surface of the housing 31, so that the drive portion 32 can be stopped at an arbitrary position in the slit 33. Incidentally, a stopper 35 for securely restricting the moving distance of the drive portion 32 is disposed on the inside surface of the housing 31.

An O-ring 34 is disposed in a gap between the outer circumferential surface of the insertion member 60 and the inner circumferential surface of a proximal end portion 56 of the sheath portion 55, so as to seal the inside of the operating unit 30; therefore, blood, for example, is prevented from flowing into the operating unit 30.

As shown in FIG. 3, the distal end portion 57 of the sheath portion 55 located at the distal end portion 22 of the catheter 20 is provided with a through-hole 58 communicated with the lumen of the sheath portion 55. The through-hole 58 ensures that the blood positively flows between the inside and the outside of the sheath portion 55 and that the blood flows assuredly into the distal end portion 22 of the catheter 20. Incidentally, the through-hole 58 is preferably spaced by not less than 1 mm from an end face of the distal end portion 57 of the sheath portion 55 along the longitudinal direction of the sheath portion 55.

The electrode 70 for measuring the cardiac action potential is in a ring form, and is fixed by caulking to the distal end portion 62 of the insertion member 60 of which the outer circumferential surface exclusive of a bevel 63A of the injection needle 63 is coated with an electric insulator 64. Incidentally, in FIG. 2, the electric insulator 64 is omitted, for simplification.

For example, between the case where the electrode 70 is present in blood and the case where the electrode 70 is in contact with a cardiac tissue, there is recognized a large change in the cardiac action potential. On the other hand, between the case where the electrode 70 is in contact with the surface of the cardiac tissue and the case where the electrode 70 is located inside the cardiac tissue, there is not generated any large change in the cardiac action potential.

Therefore, it is preferable that the electrode 70 is spaced by a distance of 1 to 3 mm from the bevel 63A of the injection needle 63 along the longitudinal direction of the insertion member 60. In this arrangement position, if a change in the cardiac action potential is measured, it indicates that the injection needle 63 is securely located inside the cardiac tissue.

The shape of the electrode 70 is not particularly limited; for example, the electrode 70 may be disposed partly along the circumferential direction. The fixation of the electrode 70 is not particularly limited; for example, the electrode 70 may be fixed by applying adhesion. The electric insulator 64 is, for example, formed of an electrically insulating material such as a polyimide varnish, a polyurethane resin, etc.

The wire 80 extending from the output terminal 50 disposed in the operating unit 30 is connected to the electrode 70. The wire 80 includes a conductor 81 having a terminal connected to the electrode 70, and an electric insulator 82 covering the conductor 81. The conductor 81 is fixed to the electric insulator 64 covering the outer circumference of the insertion member 60 by, for example, adhesion.

Namely, the electrode 70 is connected to the conductor 81 coated with the electric insulator 82, and the conductor 81 extends to the proximal end portion 21 of the catheter 20. The materials of the electrode 70 and the conductor 81 are not particularly limited, but are preferably platinum, platinum-iridium, tungsten, silver, or the like.

Incidentally, where the insertion member 60 and the injection needle 63 are separate bodies, the needle is attached after the outer circumferential surface of the insertion member 60 is coated with the electric insulator 64 and the electrode 70 and the wire 80 are disposed. In this case, the coating with the electric insulator 64 can be carried out without the need to avoid the bevel 63A of the injection needle 63, and, therefore, the coating operation is simplified. In addition, where the insertion member 60 is formed of an electric insulator such as a plastic, the coating with the electric insulator 64 is not needed.

Next, referring to FIG. 6, a catheter system 10 to which the catheter 20 is applied will be described.

The catheter system 10 includes the catheter 20, a second electrode 97 for measuring a cardiac action potential (an electrocardio), and a vital amplifier 90 for detecting a waveform change in the cardiac action potential measured by the first electrode 70. Incidentally, the second electrode 97 is provided as a separate body independent from the catheter 20.

The vital amplifier 90 includes input terminals 91 and 95, and, for example, the input terminal 91 is for a positive electrode, while the input terminal 95 is for a negative electrode. The input terminal 91 is connected through a cord 92 to the output terminal 50 of the catheter 20, and is connected through the wire 80 extending inside the sheath portion 55 to the first electrode 70 disposed at the distal end portion 62 of the insertion member 60. The input terminal 95 is connected through a cord 96 to the second electrode 97. Namely, the vital amplifier 90 is connected to the first electrode 70 and the second electrode 97. The second electrode 97 is fixed at an appropriate position on the body surface of a patient.

Therefore, when a cardiac muscle tissue is punctured by the injection needle 63 and the electrode 70 is located in contact with or in the inside of the cardiac muscle tissue, a large change is generated in the waveform of the cardiac action potential. Accordingly, with the vital amplifier 90 it is possible, for example, to judge that the waveform of the cardiac action potential has been changed due to the puncture by the injection needle when the waveform pattern of the cardiac action potential has changed more largely than a previously estimated level, and, hence, to confirm the puncture by the injection needle. Incidentally, the waveform pattern of the cardiac action potential differs depending on the part punctured.

Next, the method of using the catheter system 10 will be described, referring to the case where the target part is a cardiac tissue.

First, the operator, by use of, for example, a guiding catheter under X-ray fluoroscopy, inserts the catheter 20 into a living body, and guides the distal end portion 22 of the catheter 20 into a ventricle of heart located in the vicinity of the target tissue.

Blood under the blood pressure flows into the distal end portion 57 of the sheath portion 55, and the cardiac action potential is measured by the electrode 70 located in the vicinity of the injection needle 63. In this case, since the presence of the through-hole 58 formed in the distal end portion 57 of the sheath portion 55 promises good blood flow between the inside and the outside of the sheath portion 55, the flowing-in of the blood is assured. Therefore, it is possible to measure more accurately the cardiac action potential in the case where the electrode 70 is present in the blood.

Thereafter, the operator, while measuring the cardiac action potential by the electrode 70, presses the distal end portion 57 of the sheath portion 55 against the cardiac wall, and operates the needle control portion 40. As a result, the insertion member 60 is moved in the distal direction relative to the sheath portion 55, to protrude the injection needle 63 from the distal end portion 57 of the sheath portion 55, thereby puncturing the cardiac muscle tissue.

When the cardiac muscle tissue is punctured by the injection needle 63 and the electrode 70 is thereby moved into the inside of the cardiac muscle tissue, a large change is generated in the waveform pattern of the cardiac action potential. Therefore, the puncture by the injection needle 63 can be detected.

Then, for example, by use of a syringe connected to the hub 45, a therapeutic composition is injected into the cardiac muscle tissue through the injection needle 63. In this case, it is confirmed that no large change is generated in the waveform pattern of the cardiac action potential. This makes it possible to detect that pull-off of the injection needle 63 from the target tissue by a reaction force arising from the injection of the therapeutic composition is not generated.

After the injection is finished, the needle control portion 40 is operated so as to retract the injection needle 63 into the distal end portion 57 of the sheath portion 55, and the distal end portion 22 of the catheter 20 is moved to the next target part. Then, the above operations are repeated.

Thus, in Embodiment 1 of the present invention, it is possible, based on the cardiac action potential measured by the electrode 70, to securely puncture the target tissue by the injection needle 63 and to securely inject the therapeutic composition into the target tissue through the injection needle 63. In addition, since there is no need for a special device for fixing the catheter to the tissue, low invasiveness is ensured.

Next, a modification of the catheter 20 according to Embodiment 1 will be described.

Figure 8:
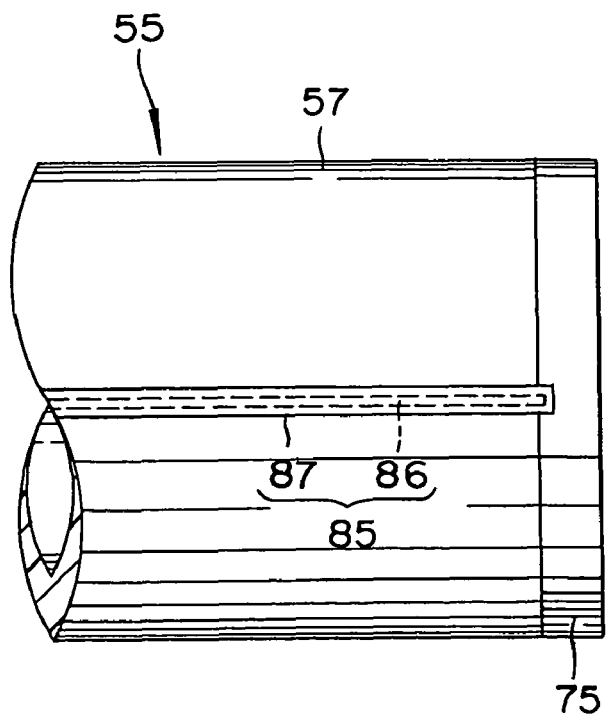
FIG. 8 is a side view of the distal end portion of the sheath portion shown in FIG. 7.
Figure 9:
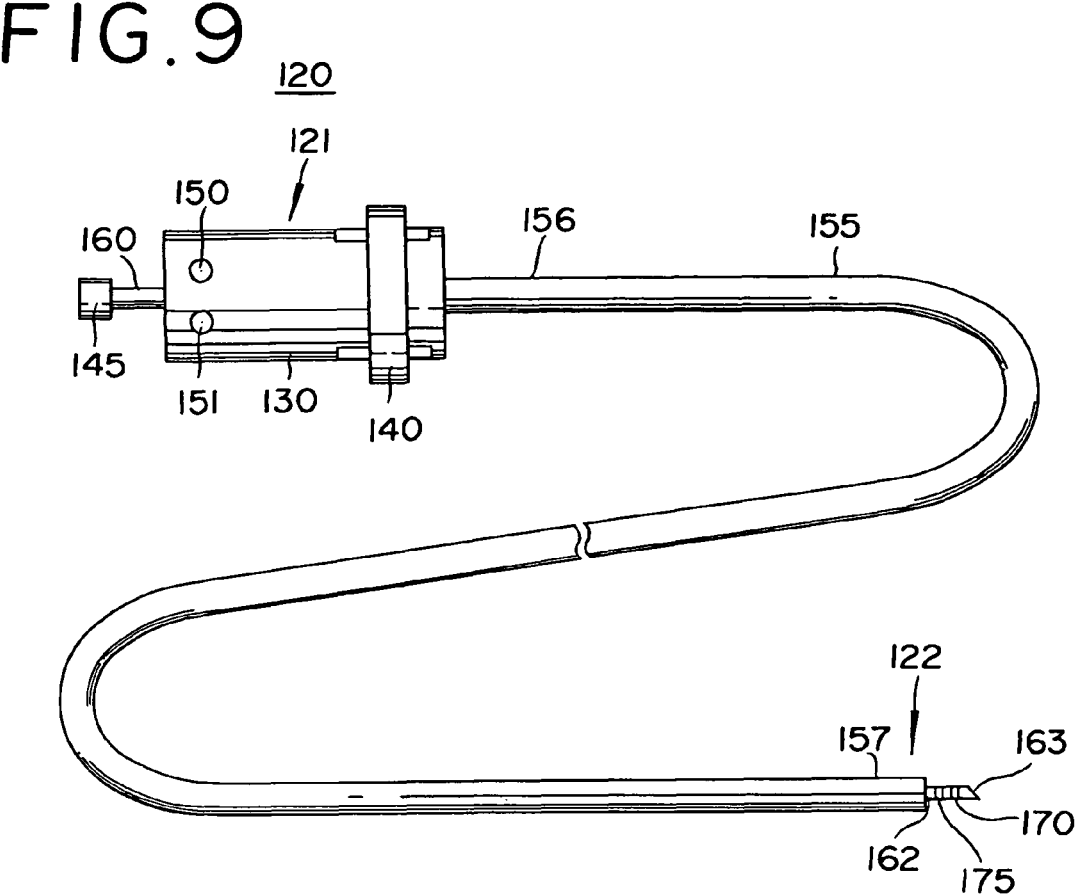
FIG. 9 is a schematic view of a catheter according to Embodiment 2.
Figure 10:
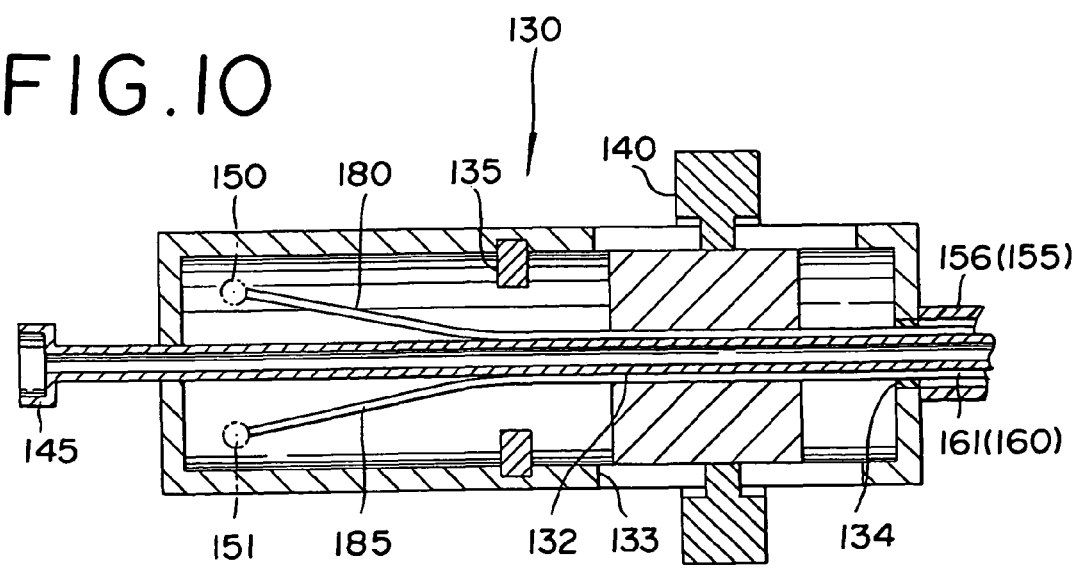
FIG. 10 is a sectional view of a proximal end portion of the catheter shown in FIG. 9.
Figure 11:
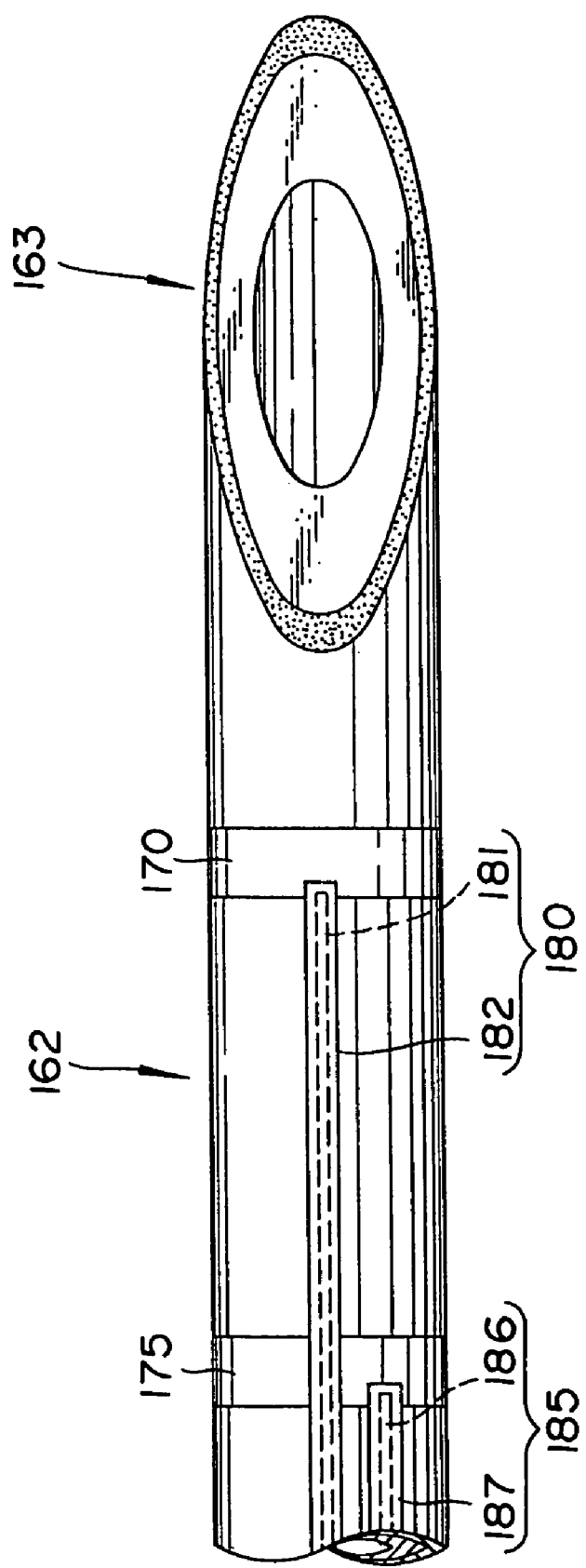
FIG. 11 is a side view for illustrating a distal end portion of an insertion member of the catheter shown in FIG. 9.

The electrode for measuring a cardiac action potential may not necessarily be disposed at the distal end portion 62 of the insertion member 60, but may be disposed at the distal end portion 57 of the sheath portion 55, as shown in FIGS. 7 and 8.

An electrode 75 is in a ring form, and is fixed to an end face of the distal end portion 57 of the sheath portion 55 by, for example, caulking. A wire 85 extending from the output terminal 50 disposed in the operating unit 30 is connected to the electrode 75.

The wire 85 includes a conductor 86 having a terminal to be connected to the electrode 75, and an electric insulator 87 covering the conductor 86. The conductor 86 is fixed to the outer circumference of the sheath portion 55 by, for example, adhesion. Where the outer circumference of the sheath portion 55 is electrically conductive, however, the conductor 86 is fixed after coating the outer circumference with an electric insulator, for example.

Incidentally, at the proximal end portion 56 of the sheath portion 55, the wire 85 is, for example, extended through the gap between the outer circumference of the proximal end portion 61 of the insertion member 60 and the inner circumferential surface of the proximal end portion 56 of the sheath portion 55, is introduced into the inside of the housing 31 of the operating unit 30, and passes through the drive portion 32.

Next, the method for using the modified example of the catheter 20 will be described.

Since the electrode 75 is disposed at the end face of the distal end portion 57 of the sheath portion 55, a large change in the waveform pattern of the cardiac action potential is generated between before and after of the contact of the distal end portion 57 of the sheath portion 55 with a cardiac muscle tissue.

For example, the catheter is inserted into a living body and advanced to the vicinity of a target tissue, and, while measuring the cardiac action potential, the distal end portion 57 of the sheath portion 55 is moved. Then, a large change is generated in the waveform of the cardiac action potential, whereby the contact of the distal end portion 57 of the sheath portion 55 with the target tissue is recognized; thereafter, the needle control portion 40 is operated so as to protrude the injection needle 63 from the distal end portion 57 of the sheath portion 55.

In this case, when a large change is generated in the waveform pattern of the cardiac action potential, it is judged that the distal end portion 57 of the sheath portion 55 has been separated from the target tissue due to a reaction force arising from the protruding operation of the injection needle 63. Therefore, by confirming the absence of a large change in the waveform pattern of the cardiac action potential during the protruding operation of the injection needle 63, it is possible to detect the assured puncture of the target tissue by the injection needle 63.

Besides, in injecting the therapeutic composition into the target tissue through the injection needle 63, the absence of a large change in the waveform pattern of the cardiac action potential is also confirmed. This makes it possible to detect that the distal end portion 57 of the sheath portion 55 has not been separated from the target tissue by a reaction force arising from the injection of the therapeutic composition, i.e., that the injection needle 63 has not been pulled out of the target tissue.

Thus, in the modified example also, it is possible to securely puncture the target tissue by the injection needle 63 and to securely inject the therapeutic composition into the target tissue through the injection needle 63.

Next, referring to FIGS. 9 to 12, a catheter 120 according to Embodiment 2 will be described. Embodiment 2 generally differs from Embodiment 1 in that a plurality of electrodes 170 and 175 functioning as a puncture sensor are provided at a distal end portion 162 of an insertion member 160 and that there is no need for an electrode independent from the catheter.

To be more specific, an operating unit 130 located at a proximal end portion 121 of the catheter 120 includes a plurality of output terminals 150 and 151. The output terminal 150 is connected to the electrode 170 disposed at a distal end portion 122 of the catheter 120, through a wire 180 extending along the insertion member 160. In other words, the electrode 170 is connected to a terminal of a conductor 181 coated with an electric insulator 182.

The output terminal 151 is connected to the electrode 175 disposed at the distal end portion 122 of the catheter 120, through a wire 185 extending along the insertion member 160. In other words, the electrode 175 is connected to a terminal of a conductor 186 coated with an electric insulator 187. The electrode 170 and the electrode 175 are spaced from each other along the longitudinal direction of the insertion member 160.

Figure 12:
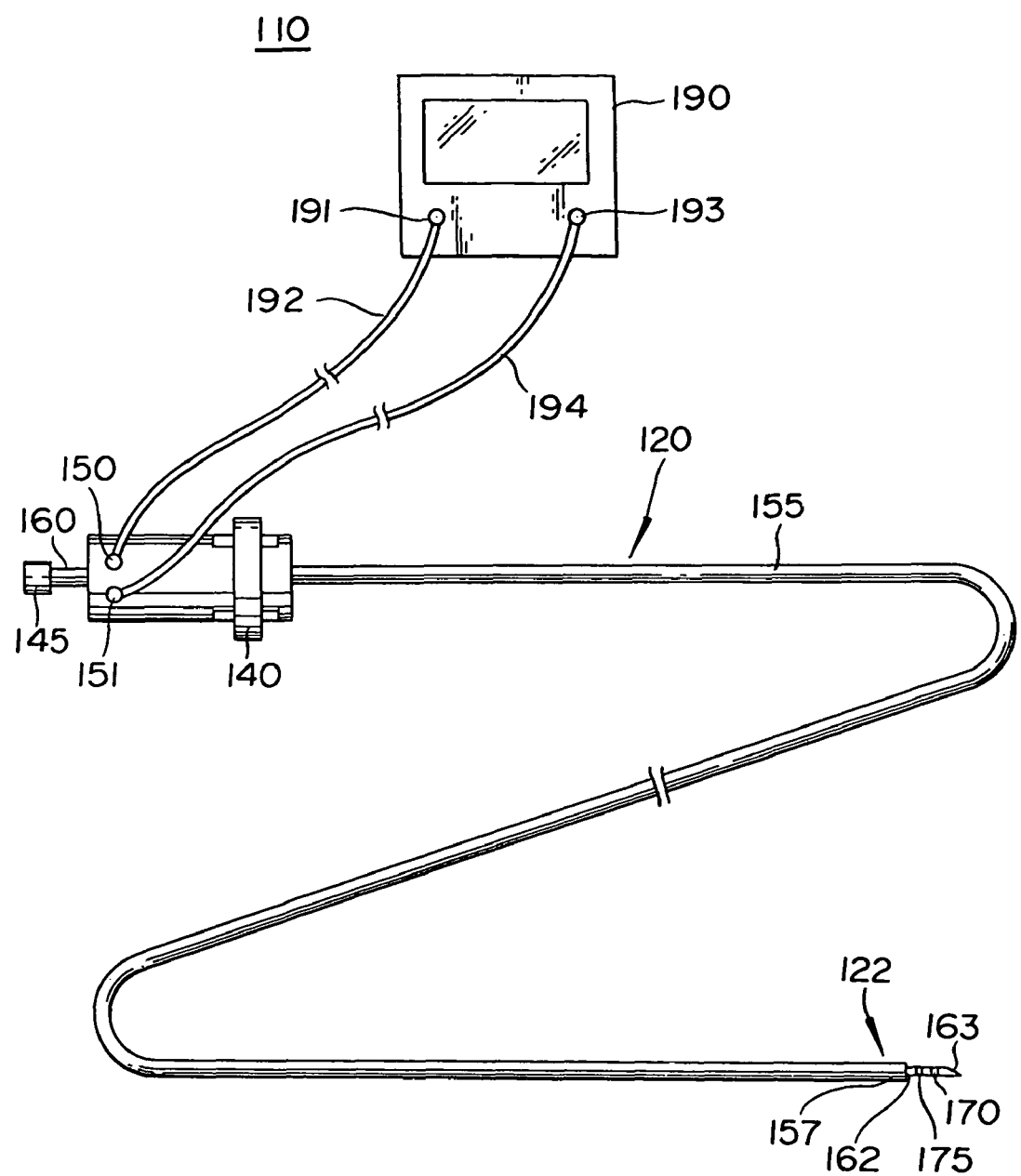
FIG. 12 is a schematic view for illustrating a catheter system to which the catheter shown in FIG. 9 is applied.

In addition, as shown in FIG. 12, a catheter system 110 to which the catheter 120 is applied includes a vital amplifier 190 for detecting the waveform pattern of a cardiac action potential measured by the electrodes 170 and 175.

The vital amplifier 190 includes, for example, an input terminal 191 for a positive electrode and an input terminal 193 for a negative electrode. The input terminal 191 is connected to the output terminal 150 of the catheter 120 through a cord 192, and is connected to the electrode 170 disposed at the distal end portion 162 of the insertion member 160 through the wire 180 extending inside a sheath portion 155.

The input terminal 193 is connected to the output terminal 151 of the catheter 120 through a cord 194, and is connected to the electrode 175 disposed at the distal end portion 162 of the insertion member 160 through the wire 185 extending inside the sheath portion 155.

Next, the method for using the catheter 120 will be described.

The catheter 120 is inserted into a living body, a distal end portion 157 of the sheath portion 155 is pressed against the cardiac wall, and a needle control portion 140 is operated. As a result, the insertion member 160 is moved in the distal direction relative to the sheath portion 155, and an injection needle 163 protrudes from the distal end portion 157 of the sheath portion 155, to puncture a cardiac muscle tissue. When the cardiac muscle tissue is punctured by the injection needle 163 and the electrode 170 is moved into the inside of the cardiac muscle tissue, a large change is generated in the waveform pattern of the cardiac action potential. Therefore, the puncture by the injection needle 163 can be detected.

Thus, in Embodiment 2 also, it is possible to securely puncture the target tissue by the injection needle 163 and to securely inject a therapeutic composition into the target tissue through the injection needle 163.

Next, referring to FIG. 13, a modification of the catheter according to Embodiment 2 will be described.

Where a plurality of electrodes are disposed at a distal end portion of the catheter, the electrode may not necessarily be disposed at the distal end portion 162 of the insertion member 160 but may be disposed at the distal end portion 157 of the sheath portion 155.

For example, an electrode 270 is in a ring form, and is fixed to an end face of the distal end portion 157 of the sheath portion 155 by, for example, caulking. A wire 280 extending from the output terminal 150 disposed in the operating unit 130 is connected to the electrode 270. The wire 280 includes a conductor 281 having a terminal to be connected to the electrode 270, and an electric insulator 282 coated on the conductor 281.

An electrode 275 is in a ring form, and is fixed, for example by caulking, at a position spaced from the electrode 270. A wire 285 extending from the output terminal 151 disposed in the operating unit 130 is connected to the electrode 275. The wire 285 includes a conductor 286 having a terminal to be connected to the electrode 275, and an electric insulator 287 coated on the conductor 286.

Thus, in this configuration, in the same manner as in the modified example of the catheter 20 according to Embodiment 1, a large change in the waveform pattern of the cardiac action potential is generated between before and after the contact of the distal end portion 157 of the sheath portion 155 with the cardiac muscle tissue. Therefore, it is possible to securely puncture a target tissue by the injection needle 163 and to securely inject a therapeutic composition into the target tissue through the injection needle 163.

Figure 14:
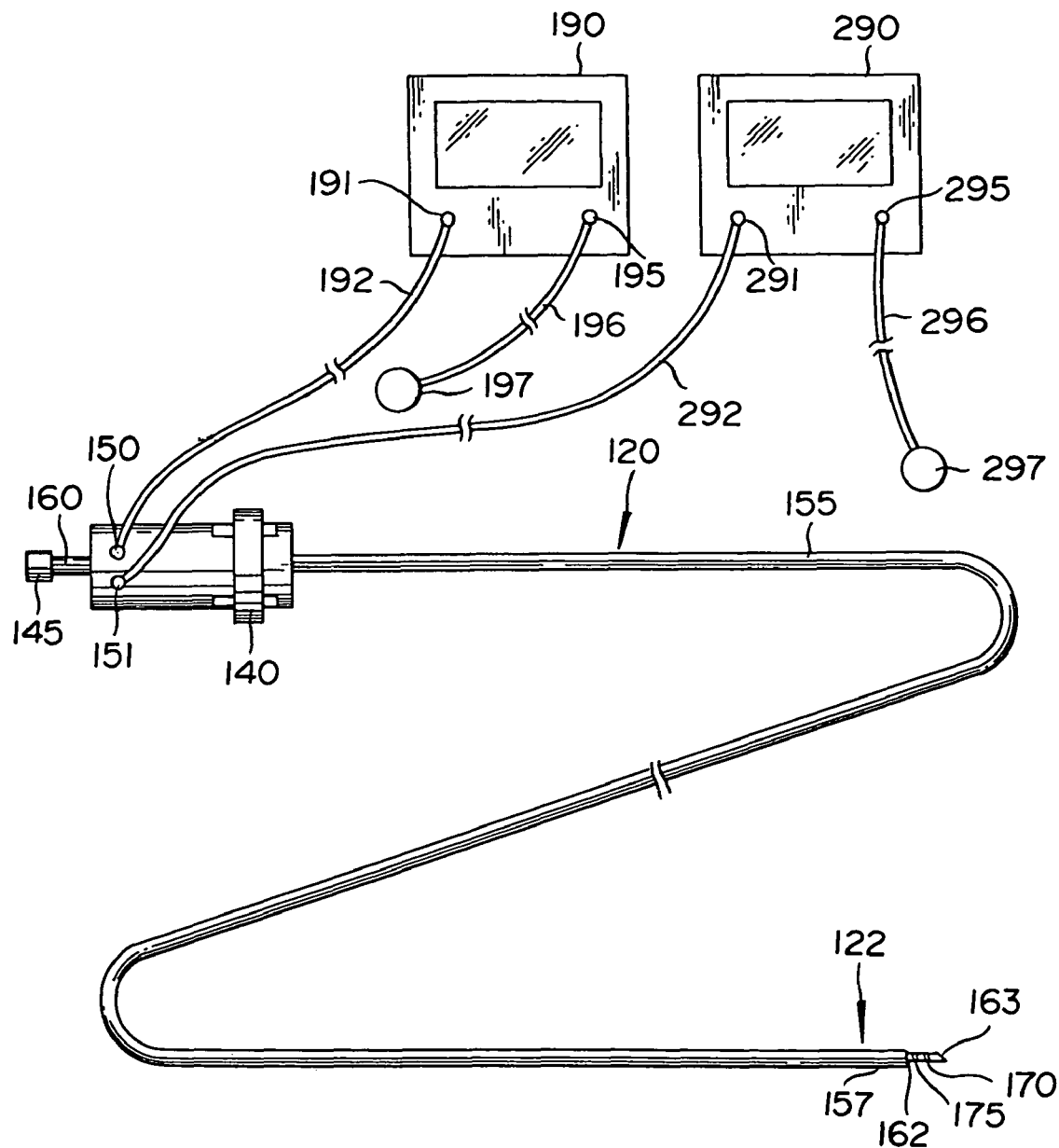
FIG. 14 is a schematic view for illustrating a modification of the catheter system to which the catheter shown in FIG. 9 is applied.

Next, referring to FIG. 14, a modified configuration of the catheter system to which the catheter 120 is applied will be described. The catheter system 210 includes a plurality of vital amplifiers 190 and 290 for detecting the waveform pattern of a cardiac action potential measured by the electrodes 170 and 175.

The vital amplifier 190 includes, for example, an input terminal 191 for a positive electrode and an input terminal 195 for a negative electrode. The input terminal 191 is connected to the output terminal 150 of the catheter 120 through a cord 192, and is connected to the electrode 170 disposed at the distal end portion 162 of the insertion member 160 through the wire 180 extending inside the sheath portion 155. The input terminal 195 is connected through a cord 196 to a second electrode 197 separate from the catheter 120.

The vital amplifier 290 includes, for example, an input terminal 291 for a positive electrode and an input terminal 295 for a negative electrode. The input terminal 291 is connected to the output terminal 151 of the catheter 120 through a cord 292, and is connected to the electrode 175 disposed at the distal end portion 162 of the insertion member 160 through the wire 185 extending inside the sheath portion 155. The input terminal 295 is connected through a cord 296 to a second electrode 297 separate from the catheter 120.

The electrode 170 and the electrode 175 are spaced from each other along the longitudinal direction of the insertion member 160. Therefore, as the puncture depth of the injection needle 164 into a tissue increases, the waveform pattern of a cardiac action potential measured by the electrodes 170 and 175 varies sequentially. In other words, the puncture depth of the injection needle 164 can be detected.

Next, the method for using the catheter 120 in the catheter system 210 will be described.

The catheter 120 is inserted into a living body, the distal end portion 157 of the sheath portion 155 is pressed against the cardiac wall, and the needle control portion 140 is operated. As a result, the insertion member 160 is moved in the distal direction relative to the sheath portion 155, and the injection needle 163 protrudes from the distal end portion 157 of the sheath portion 155, to puncture the cardiac muscle tissue. When the cardiac muscle tissue is punctured by the injection needle 163 and the electrode 170 is moved into the inside of the cardiac muscle tissue, a large change is generated in the waveform pattern of the cardiac action potential confirmed by the amplifier 190. Therefore, the puncture by the injection needle 163 can be detected.

In this case, if a large change is not generated in the waveform pattern of the cardiac action potential which is measured by the electrode 175 and confirmed by the amplifier 290, it is judged that the puncture depth of the injection needle 163 is located at an intermediate position between the electrode 170 and the electrode 175. In addition, when the puncture by the injection needle 163 is further advanced and the electrode 175 is moved into the inside of the cardiac tissue, a large change is generated in the waveform pattern confirmed by the amplifier 290. Therefore, if a large change is generated in the waveform pattern of the cardiac action potential which is measured by the electrode 175 and confirmed by the amplifier 290, it is judged that the puncture depth of the injection needle 163 exceeds the position of the electrode 175.

In other words, by appropriately changing the arrangement positions and the number of the electrodes, it is possible to accurately detect the puncture depth of the injection needle 163. Therefore, it is possible to prevent the injection needle 163 from protruding more than expected so as, for example, to pierce through a cardiac wall or to puncture to a depth different from a target depth in a diseased part.

Thus, with the catheter 120 according to Embodiment 2, it is possible to detect the puncture depth of the injection needle, whereby the puncture by the injection needle 163 is further assured. Besides, this system is particularly suited to a therapy in which an accurate puncture by the injection needle 163 to a target depth in a diseased part is required for attaining the effect of the therapy.

Next, referring to FIG. 15, a catheter according to Embodiment 3 will be described. Embodiment 3 generally differs from Embodiment 2 in that the catheter includes an electrode 370 disposed at a distal end portion 362 of an insertion member 360, and an electrode 375 disposed at a distal end portion 357 of a sheath portion 355.

To be more specific, the electrode 370 is in a ring form, the outer circumferential surface of the distal end portion 362 of the insertion member 360 exclusive of a bevel 363A of an injection needle 363 is coated with an electric insulator 364, and the electrode 370 is fixed to the distal end portion 362 of the insertion member 360 by caulking.

A wire 380 extending from an output terminal disposed in the operating unit is connected to the electrode 370. The wire 380 includes a conductor 381 having a terminal connected to the electrode 370, and an electric insulator 382 covering the conductor 381. The conductor 381 is fixed, for example by adhesion, to the electric insulator 364 covering the outer circumference of the insertion member 360.

The electrode 375 disposed at an end face of the distal end portion 357 of the sheath portion 355 is in a ring form, and is fixed by caulking, for example. A wire 385 extending from an output terminal disposed in the operating unit (this output terminal is different from the one to which the electrode 370 is connected) is connected to the electrode 375.

The wire 385 includes a conductor 386 having a terminal connected to the electrode 375, and an electric insulator 387 covering the conductor 386. The conductor 386 is fixed, for example by adhesion, to the outer circumference of the sheath portion 355.

Next, the method for using the catheter according to Embodiment 3 will be described.

First, the catheter is inserted into a living body and advanced to the vicinity of a target tissue, and, while measuring a cardiac action potential, the distal end portion 357 of the sheath portion 355 is moved. Then, a large change is generated in the waveform pattern of a cardiac action potential measured by the electrode 375, whereby the contact of the distal end portion 357 of the sheath portion 355 with the target tissue can be confirmed; thereafter, the needle control portion is operated so as to protrude the injection needle 363 from the distal end portion 357 of the sheath portion 355.

In this case, where a large change is generated in the waveform pattern of the cardiac action potential measured by the electrode 375, it is judged that the distal end portion 357 of the sheath portion 355 has been separated from the target tissue by a reaction force arising from the protruding operation of the injection needle 363. Therefore, the operator confirms the absence of a large change in the waveform pattern of the cardiac action potential measured by the electrode 375, during the protruding operation of the injection needle 363.

On the other hand, when a cardiac muscle tissue is punctured by the injection needle 363 and the electrode 370 is moved into the inside of the cardiac muscle tissue, a large change is generated in the waveform pattern of a cardiac action potential measured by the electrode 370. Therefore, the puncture by the injection needle 363 can be detected.

Besides, in injecting a therapeutic composition into the target tissue through the injection needle 363, also, the absence of a large change in the waveform pattern of the cardiac action potential measured by the electrodes 370 and 375 is confirmed. This makes it possible to detect that the distal end portion 357 of the sheath portion 355 has not been separated from the target tissue by a reaction force arising from the injection of the therapeutic composition and that the injection needle 363 has not been pulled out of the target tissue.

Thus, in the catheter according to Embodiment 3, the reliability as to the puncture of a target tissue by the injection needle and as to the injection of a therapeutic composition is enhanced.

Next, referring to FIG. 16, a catheter system according to Embodiment 4 will be described. Embodiment 4 generally differs from Embodiment 3 in that a plurality of electrodes 470 and 471 functioning as a puncture sensor are disposed at a distal end portion 462 of an insertion member 460.

The electrode 470 is disposed adjacently to a bevel of an injection needle 463, and the electrode 471 is disposed at a position spaced from the electrode 470 along the longitudinal direction of the insertion member 460. An electrode 475 disposed at a distal end portion 457 of a sheath portion 455 is disposed at a position spaced to the proximal end side from an end face of the distal end portion 457.

In addition, the catheter system according to Embodiment 4 includes a plurality of vital amplifiers 490A and 490B, according to the configuration of the electrodes 470, 471, and 475 disposed at the distal end portion of the catheter. The vital amplifier 490A includes an input terminal 491A (for a positive electrode, for example) connected to the electrode 470, and an input terminal 493A (for a negative electrode, for example) connected to the electrode 475. The vital amplifier 490B includes an input terminal 491B (for a positive electrode, for example) connected to the electrode 471, and an input terminal 493B (for a negative electrode, for example) connected to the electrode 475. Namely, the electrode 475 is connected to both of the vital amplifiers 490A and 490B.

In the above configuration, when a target tissue is punctured by the injection needle 463 and the electrode 470 is brought into contact with or moved into the inside of the target tissue, a large change is generated in the waveform pattern of a cardiac action potential measured by the vital amplifier 490A. Therefore, the puncture by the injection needle 463 can be detected.

In addition, when the puncture depth of the injection needle 463 increases and the electrode 471 is brought into contact with or moved into the inside of the target tissue, a large change is generated in the waveform pattern of a cardiac action potential measured by the vital amplifier 490B. Therefore, it is possible to detect the puncture depth of the injection needle 463 and, hence, to render the puncture by the injection needle further assured.

Next, referring to FIG. 17, a catheter system according to Embodiment 5 will be described. Embodiment 5 generally differs from Embodiment 3 in that a plurality of electrodes 570 and 571 are disposed at a distal end portion 562 of an insertion member 560 and that a plurality of electrodes 575 and 576 are disposed at a distal end portion 557 of a sheath portion 555.

The electrode 570 is disposed adjacently to a bevel of an injection needle 563, and the electrode 571 is disposed at a position spaced from the electrode 570 along the longitudinal direction of the insertion member 560. The electrode 575 is disposed at an end face of the distal end portion 557 of the sheath portion 555, and the electrode 576 is disposed at a position spaced to the proximal end side from an end face of the distal end portion 557.

In addition, the catheter system according to Embodiment 5 includes a plurality of vital amplifiers 590A and 590B, according to the configuration of the electrodes 570, 571, 575, and 576 disposed at a distal end portion of the catheter. The vital amplifier 590A includes an input terminal 591A (for a positive electrode, for example) connected to the electrode 570, and an input terminal 593A (for a negative electrode, for example) connected to the electrode 571. The vital amplifier 590B includes an input terminal 591B (for a positive electrode, for example) connected to the electrode 575, and an input terminal 593B (for a negative electrode, for example) connected to the electrode 576.

In the above configuration, when the distal end portion 557 of the sheath portion 555 comes into contact with a target tissue, a large change is generated in the waveform pattern of a cardiac action potential measured by the vital amplifier 590B. Then, when the target tissue is punctured by the injection needle 563 and the electrode 570 is brought into contact with or moved into the inside of the target tissue, a large change is generated in the waveform pattern of a cardiac action potential measured by the vital amplifier 590A. Therefore, the puncture by the injection needle 563 can be detected.

Besides, in puncturing by the injection needle 563, if a large change is generated in the waveform pattern of a cardiac action potential measured by the vital amplifier 590B, it can be detected that the distal end portion 557 of the sheath portion 555 has been separated from the target tissue by a reaction force arising from the protruding operation of the injection needle 563. Similarly, in injecting a therapeutic composition, if a large change is generated in the waveform pattern of a cardiac action potential measured by the vital amplifier 590B, it can be detected that the distal end portion 557 of the sheath portion 555 has been separated from the target tissue by a reaction force arising from the injection of the therapeutic composition.

Thus, in Embodiment 5, the reliability as to the puncture of a target tissue by the injection needle and as to the injection of a therapeutic composition is enhanced.

Next, referring to FIG. 18, a modification of the catheter system according to Embodiment 5 will be described. This modified example differs from the catheter system of Embodiment 5 in the position of arrangement of the electrode 575 at the distal end portion 557 of the sheath portion 555 and in the method of connection between the electrodes 571, 575 and the vital amplifiers 590A, 590B.

That is to say, the electrode 575 is disposed at a position spaced from an end face of the distal end portion 557 of the sheath portion 555. The electrode 571 is connected to the input terminal 591B of the vital amplifier 590B. The electrode 575 is connected to the input terminal 593A of the vital amplifier 590A.

In the above configuration, when a target tissue is punctured by the injection needle 563 and the electrode 570 is brought into contact with or moved into the inside of the target tissue, a large change is generated in the waveform pattern of a cardiac action potential measured by the vital amplifier 590A. Therefore, the puncture by the injection needle 563 can be detected.

In addition, when the puncture depth of the injection needle 563 increases and the electrode 571 is brought into contact with or moved into the inside of the target tissue, a large change is generated in the waveform pattern of a cardiac action potential measured by the vital amplifier 590B. Therefore, it is possible to detect the puncture depth of the injection needle 563 and, hence, to render the puncture by the injection needle 563 further assured.

Figure 13:
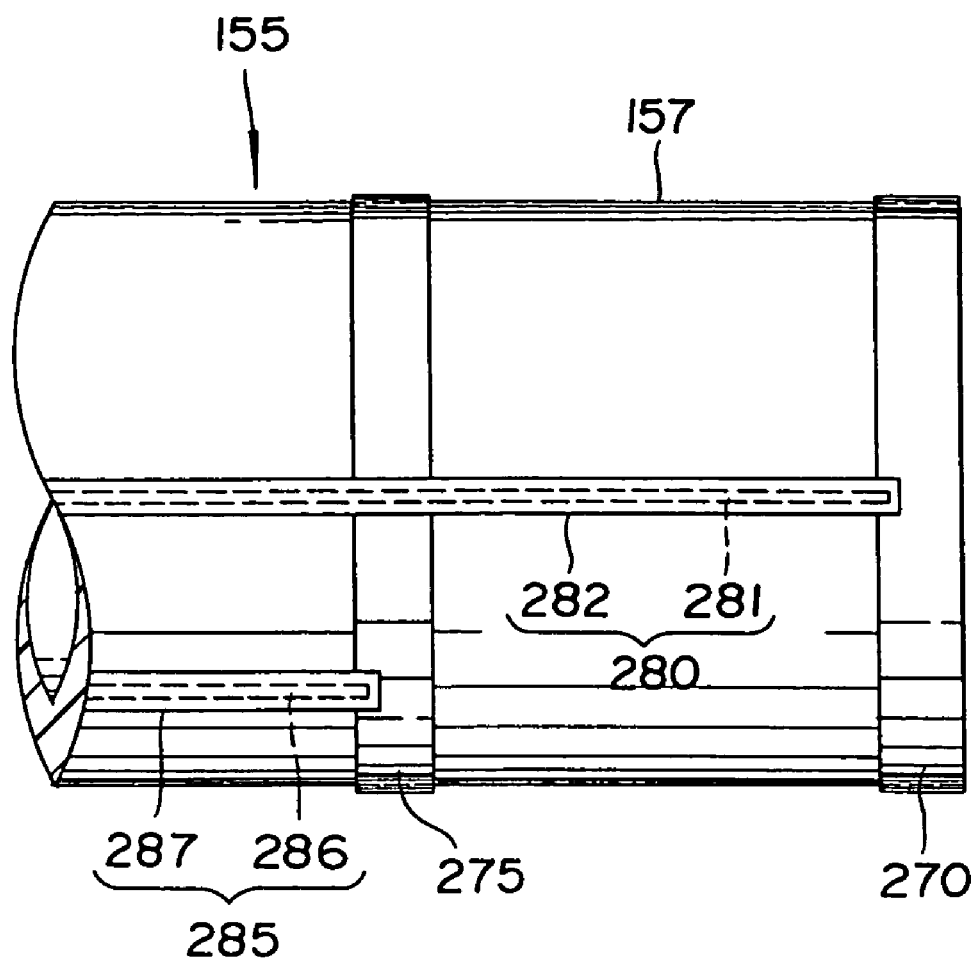
FIG. 13 is a side view of a distal end portion of a sheath portion, for illustrating a modification of the catheter according to Embodiment 2.
Figure 19:
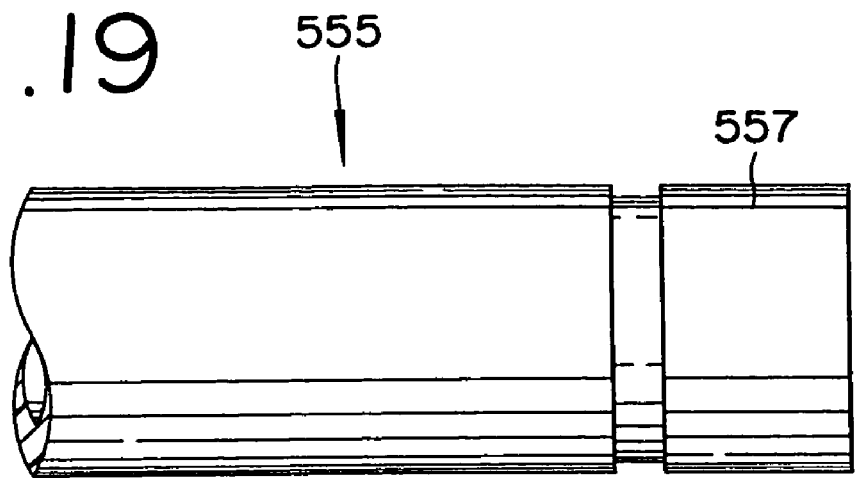
FIG. 19 is a side view of a distal end portion of a sheath portion, for illustrating another modification of the catheter shown in FIGS. 13, 16, 17, and 18.

The electrode or electrodes disposed at positions spaced to the proximal end side from the end face of the sheath portion 555, such as the electrode 576 shown in FIGS. 17 and 18, inclusive of the electrode 275 shown in FIG. 13 and the electrode 475 shown in FIG. 16, may be embedded in the distal portion 557 of the sheath portion 555, as shown in FIG. 19. Such a configuration can be obtained, for example, by providing the distal end portion 557 of the sheath portion 555 with a recessed portion along the circumferential direction, fitting the electrode into the recessed portion by caulking, connecting a conductor, which extends to a proximal end portion of the catheter, to the electrode, and coating the surface of the conductor with an electric insulator.

Figure 20:
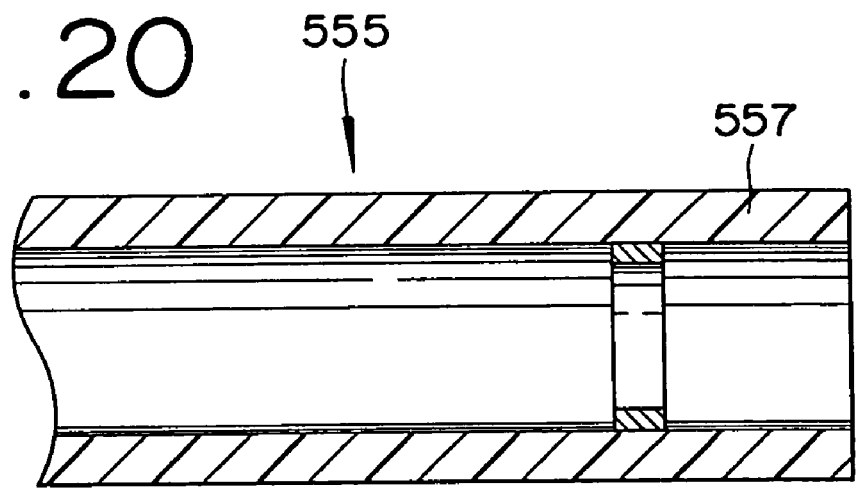
FIG. 20 is a sectional view of a distal end portion of a sheath portion, for illustrating a modification different from that shown in FIG. 19.

Furthermore, as shown in FIG. 20, the electrode or electrodes may be disposed and fixed in the lumen of the sheath portion 555. This configuration can be obtained, for example, by inserting an electrode, which has an outside diameter slightly smaller than the inside diameter of the lumen of the sheath portion 555, into the lumen of the sheath portion 555, and fixing the electrode by adhesion at a position spaced by several millimeters from the end face of the distal end portion 557 of the sheath portion 555 along the longitudinal direction of the sheath portion 555.

In the case where the electrode or electrodes are embedded or disposed and fixed in the inside of the lumen, it is advantageous in view of that it is possible to restrain measurement errors from being generated due, for example, to an erroneous contact of the electrode with a rugged portion of the surface of a ventricle of heart.

Next, referring to FIGS. 21 to 23, one example of the method of manufacturing a sheath portion and an insertion member at which electrodes are disposed will be described.

As a sheath portion 655, there is used a polyimide tube with braided wire therein (a product by Microlumen) containing tungsten carbide which functions as a x-ray contrast marker. The polyimide tube has a three-layer structure in which the braided wire is sandwiched between inner and outer polyimide layers, and has a length of 1300 mm, an outside diameter of 1.0 mm, and an inside diameter of 0.9 mm.

One end (distal end portion) of the polyimide tube is subjected to laser processing to strip only the outermost polyimide layer from a portion of about 2 mm, whereby the braided wire is exposed.

Then, as shown in FIG. 21, a distal end cap 657 is attached to the distal end portion of the polyimide tube. The distal end cap 657 is formed of SUS304 in a truncated conical shape, and the inside and outside surfaces thereof are covered with an electric insulator.

The distal end of the distal end cap 657 has an outside diameter of 1.8 mm, and the portion of the distal end cap 657 for attachment to the polyimide tube has an outside diameter of 1.2 mm and a length of 3 mm. An electrode 675 for measuring a cardiac action potential is composed of an annular portion located on the inside of an electric insulator 687.

The other end (proximal end portion) of the polyimide tube is subjected to laser processing to strip only the outermost polyimide layer, whereby the braided wire is exposed. Then, as shown in FIG. 23, a connector 686 is attached to that portion of the other end 656 of the polyimide tube at which the braided wire is exposed.

A wire 685 extending from an output terminal 651 disposed in the operating unit is connected to the connector 686. Incidentally, in the inside of the connector 681, the braided wire is connected to the conductor of the wire 685. Besides, the wire 685 extends through a through-hole formed in a drive portion 632.

As an insertion member 660, there is used a hollow steel pipe (a product by OHBAKIKO CO., LTD) of which the inside and outside surfaces are coated with a polyimide varnish (electric insulator). The hollow steel pipe is formed of SUS304, and has a length of 1500 mm, an outside diameter of 0.7 mm, and an inside diameter of 0.5 mm.

As shown in FIG. 22, a distal end portion 662 of the insertion member 660 is polished to form a bevel 670 which constitutes a cutting edge surface. An electrode for measuring a cardiac action potential is composed of the annular portion at which the insulating coating of polyimide is stripped (the annular portion located at an intermediate position between an electric insulator 664 and an electric insulator 682).

A proximal end portion 661 of the insertion member 660 is subjected to stripping of only the outermost polyimide layer at an appropriate portion beyond the drive portion 632 so as to expose the braided wire. Then, as shown in FIG. 23, the connector 681 is attached to the portion at which the braided wire is exposed. A wire 680 extending from an output terminal 650 disposed in the operating unit is connected to the connector 681. Incidentally, in the inside of the connector 681, the braided wire is connected to a conductor of the wire 680.

In this manner, the electrodes for measuring the cardiac action potential can be disposed at the distal end portion of the insertion member 660 and the distal end portion of the sheath portion 655.

Figure 24:
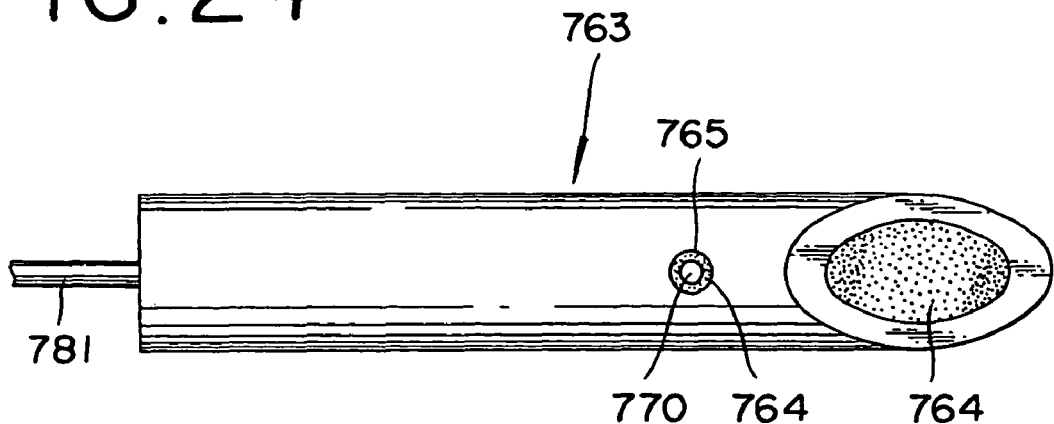
FIG. 24 is a side view for illustrating an injection needle applied to an animal experiment for verifying the detection of puncture through measurement of a cardiac action potential.
Figure 25:
FIG. 25 is a waveform diagram for illustrating the results of verification upon the animal experiment, showing the case where an electrode at the injection needle is present in blood.

Next, referring to FIGS. 24 to 26, the results of an animal experiment for verifying the detection of puncture through measurement of a cardiac action potential will be described.

An injection needle 763 used for puncture was formed as follows. First, a stainless steel hollow needle was provided with a side hole 765. The hollow needle had an outside diameter of 0.6 mm and an inside diameter of 0.3 mm. The position of the side hole 765 was spaced by 10 mm from the tip end of a bevel of the hollow needle along the longitudinal direction of the hollow needle.

Then, a conductor 781 was inserted into the lumen of the hollow needle via the side hole 765, and was drawn out from a proximal end portion of the hollow needle. The conductor had a diameter of 0.08 mm. In this condition, a polyurethane resin was potted in the lumen of the hollow needle, whereby the conductor 781 was fixed in the lumen of the hollow needle 781.

Thereafter, the conductor 781 and the polyurethane resin protruding from the side hole 765 of the hollow needle were cut. Then, the outer circumferential surface in the vicinity of the side hole 765 of the hollow needle and the cut-sectional surface were smoothened by filing. As a result, the electrode 770 composed of the cut sectional surface of the conductor 781 and the electric insulator 764 made of the polyurethane resin surrounding the electrode 770 and the conductor 781 were formed. In this manner, an injection needle 763 to be applied to an animal experiment was obtained.

Next, the details of the animal experiment will be described.

First, a pig as a specimen was subjected to muscular injection of atropine, azaperone, and ketamine and to inhalation of fluothane, whereby the pig was anesthetized. Then, the windpipe was incised, thereafter intubation was conducted, and, while maintaining respiration by a ventilator, thoracotomy was conducted, to expose the heart.

The conductor 781 extending from the injection needle 76-3 was connected to the negative-electrode input terminal of a vital amplifier, and a separate electrode for contact with the body surface was connected to the positive-electrode terminal of the vital amplifier, to enable measurement of the cardiac action potential. Incidentally, the vital amplifier used was a poly-amplifier produced by NIHON KOHDEN CORPORATION.

Thereafter, in order to check the thickness of the cardiac wall, a cardiac tissue was punctured by a test needle from the outside of the heart, and the test needle was gradually advanced deep. When the distal end of the test needle had reached the ventricle of heart and blood had flowed out from the proximal end portion of the test needle, the position was marked. Then, the test needle was pulled out, and the length from the distal end of the test needle to the marked position was measured, whereby the approximate thickness of the cardiac wall was checked.

Next, a portion in the vicinity of the puncture trace formed by the test needle was punctured by the injection needle 763, whereby the waveform pattern of the cardiac action potential under the condition where the electrode 770 was present in the cardiac tissue was recorded. Then, the puncture depth of the injection needle 763 was increased further, whereby the waveform pattern of the cardiac action potential under the condition where the electrode 770 was located at the boundary between the tissue and the blood was recorded.

Thereafter, the puncture depth of the injection needle 763 was increased further, whereby the waveform pattern of the cardiac action potential under the condition where the electrode 770 is present in the blood in the ventricle of heart was recorded.

Figure 26:
FIG. 26 is a waveform diagram for illustrating the results of verification upon the animal experiment, showing the case where the electrode at the injection needle is present in a cardiac tissue.

The waveform pattern of the cardiac action potential varied largely between the case where the electrode 770 was present in the blood (see FIG. 25) and the case where the electrode 770 was present in the cardiac tissue (see FIG. 26). Incidentally, no substantial change in the waveform pattern was recognized between the case where the electrode 770 was located at the boundary between the tissue and the blood and the case where the electrode 770 was present in the cardiac tissue.

In this manner, it was confirmed that a change in the waveform pattern of the cardiac action potential is generated between the case where the electrode is present in blood and the case where the electrode is in contact with the tissue or present in the tissue. In other words, it was verified that the puncture by the injection needle can be detected by use of the electrode disposed at the distal end portion of the catheter.

The catheter 10 as above-described is applied, for example, to gene therapy or cellular therapy.

The gene therapy is a therapy of, for example, an ischemic cardiac disease, and the injection of a gene-therapeutic composition (for example, a composition containing a nucleic acid) by use of an injection needle incorporated in a catheter is advantageous in view of low invasiveness.

The cellular therapy is a therapy for improving cardiac functions by externally implanting new cells (cardiac muscle cells, skeletal muscle blast cells, smooth muscle cells, bone marrow-derived cells, peripheral blood stem cells, cord blood-derived cells). Therefore, the injection needle incorporated in the catheter can be applied, for example, to implantation of bone marrow-derived cells to an infarction part or the surroundings thereof.

In addition, the action potential of a cardiac tissue differs between a sound state and a dead or functionally incompetent state. Therefore, by measuring the action potential, it is possible to determine an abnormal part, for example, a infarction part, of the cardiac tissue. Namely, an abnormal part of the cardiac tissue can be identified by use of an electrode disposed at a distal end portion of a catheter. Accordingly, by injecting a therapeutic composition into the determined abnormal part and the surroundings thereof, a high therapeutic effect can be expected.

In addition, the application of the present invention is not limited to cardiac diseases; for example, the invention can be applied also to a therapy for neogenesis of a blood vessel in a lower leg portion.

While the preferred embodiments of the present invention have been described using specific terms, such description is for illustrative purposes only, and it is to be understood that changes and variations may be made without departing from the spirit or scope of the following claims.

The entire disclosure of Japanese Patent Application No. 2003-90225 filed on Mar. 28, 2003 including specification, claims, drawings, and summary are incorporated herein by reference in its entirety.

What is claimed is:

1. A catheter to be percutaneously inserted into a living body lumen, said catheter comprising:
   a sheath portion having a lumen extending therein,
   an insertion member slidably disposed in said lumen of said sheath portion and having a distal end portion capable of protruding from a distal end portion of said sheath portion, an injection needle defining a distalmost end of said insertion member for injecting a therapeutic composition into a target tissue in a living body, and
   an electrode, separate and distinct from both said insertion member and said injection needle, said electrode being fixedly secured to an external surface of said distal end portion of said insertion member and spaced a predetermined distance from a bevel of said injection needle for measuring a cardiac action potential.

2. The catheter as set forth in claim 1, wherein said target tissue is a cardiac tissue.

3. The catheter as set forth in claim 1, wherein said therapeutic composition contains a nucleic acid, a protein, or cells.

4. The catheter as set forth in claim 1, wherein said distal end portion of said sheath portion is provided with a through-hole communicated with said lumen.

5. The catheter as set forth in claim 4, wherein said through-hole is spaced by not less than 1 mm from an end face of said distal end portion of said sheath portion along the longitudinal direction of said sheath portion.

6. The catheter as set forth in claim 1, wherein a plurality of said electrodes are provided.

7. The catheter as set forth in claim 1, further comprising a second electrode disposed at said distal end portion of said sheath portion for measuring a cardiac action potential.

8. The catheter as set forth in claim 1, wherein said electrode is located at an outer circumferential surface of said distal end portion of said insertion member.

9. The catheter as set forth in claim 6, wherein said electrodes are disposed at said distal end portion of said insertion member in the state of being spaced from each other along the longitudinal direction of said insertion member.

10. The catheter as set forth in claim 1, wherein said electrode disposed at said distal end portion of said insertion member is spaced by not less than 1 mm from the bevel of said injection needle along the longitudinal direction of said insertion member.

11. The catheter as set forth in claim 1, wherein said injection needle defining the distalmost end of said insertion member is formed as part of said insertion member.

12. The catheter as set forth in claim 1, wherein said injection needle defining the distalmost end of said insertion member is a separate component.

13. A catheter system comprising:
   a catheter to be percutaneously inserted into a living body lumen, said catheter comprising a sheath portion having a lumen extending therein, an insertion member slidably disposed in said lumen of said sheath portion and having a distal end portion capable of protruding from a distal end portion of said sheath portion, and an injection needle disposed at said distal end portion of said insertion member for injecting a therapeutic composition into a target tissue in a living body;
   a first electrode, separate and distinct from both said insertion member and said injection needle, fixedly secured to an external surface of said distal end portion of said insertion member, and spaced a predetermined distance from a bevel of said injection needle for measuring a cardiac action potential;

a second electrode for measuring said cardiac action potential; and a puncture detection unit to which a conductor extending from said first electrode and a conductor extending from said second electrode are connected and which detects the puncture by said injection needle based on said cardiac action potential measured by said first electrode and said second electrode.

14. The catheter system as set forth in claim 13, wherein said second electrode is disposed at a distal end portion of said catheter, and is located on the side of the proximal end of said catheter relative to said first electrode.

15. The catheter system as set forth in claim 13, wherein said second electrode is provided as a separate body independent from said catheter.

16. A method of injecting a therapeutic composition by use of a catheter to be percutaneously inserted into a living body lumen, said catheter comprising a sheath portion having a lumen extending therein, an insertion member slidably disposed in said lumen of said sheath portion and having a distal end portion capable of protruding from a distal end portion of said sheath portion, an injection needle disposed at said distal end portion of said insertion member for injecting said therapeutic composition into a target tissue, and a first electrode, separate and distinct from both said insertion member and said injection needle, said first electrode being fixedly secured to an external surface of said distal end portion of said insertion member and spaced a predetermined distance from a bevel of said injection needle for measuring a cardiac action potential, said method comprising the steps of:
(a) inserting said catheter into a living body and advancing said catheter to the vicinity of said target tissue; and
(b) puncturing said target tissue by said injection needle and injecting said therapeutic composition into said target tissue through said injection needle, based on said cardiac action potential measured by said first electrode spaced the predetermined distance from a bevel of said injection needle.

17. The method as set forth in claim 16, wherein
said step (b) comprises the steps of: moving said insertion member in the distal direction relative to said sheath portion to thereby protruding said injection needle from said distal end portion of said sheath portion, thereby puncturing said target tissue by said injection needle, while measuring said cardiac action potential by said first electrode; and injecting said therapeutic composition into said target tissue through said injection needle, after a change is detected in said cardiac action potential measured by said first electrode.

18. The method as set forth in claim 16, wherein
said catheter further comprises a second electrode disposed at said distal end portion of said sheath portion, and said step (b) comprises the steps of:

bringing said distal end portion of said sheath portion into contact with said target tissue while measuring said cardiac action potential by said second electrode;

detecting a change in the cardiac action potential measured by the second electrode;

moving said insertion member in the distal direction relative to said sheath portion to thereby protrude said injection needle from said distal end portion of said sheath portion, thereby puncturing said target tissue by said injection needle, while further measuring said cardiac action potential by said second electrode, after the change is detected in said cardiac action potential measured by said second electrode; and injecting said therapeutic composition into said target tissue through said injection needle, after it is confirmed that no change is generated in said cardiac action potential measured by said second electrode and said first electrode while moving the insertion member in the distal direction.

* * * * *